United States Patent
Bissinger et al.

Patent Number: 5,371,061
Date of Patent: Dec. 6, 1994

[54] HERBICIDAL PICOLINAMIDE DERIVATIVES

[75] Inventors: Hans-Joachim Bissinger, Amsterdam, Netherlands; Axel Kleemann, Hanau; Richard J. G. Searle, Schwabenheim, both of Germany

[73] Assignee: American Cyanamid Company, Wayne, N.J.

[21] Appl. No.: 939,756

[22] Filed: Sep. 2, 1992

[30] Foreign Application Priority Data

Sep. 13, 1991 [EP] European Pat. Off. ........ 91115545.5

[51] Int. Cl.$^5$ .................... C07P 213/02; A01N 43/40
[52] U.S. Cl. .................... 504/130; 544/124; 546/14; 546/193; 546/194; 546/256; 546/261
[58] Field of Search ........... 546/194, 256, 261, 14.193; 544/124; 504/130

[56] References Cited

FOREIGN PATENT DOCUMENTS 3804346 8/1989 Germany .................. 546/256

Primary Examiner—C. Warren Ivy
Assistant Examiner—Zinna N. Davis
Attorney, Agent, or Firm—Michael P. Morris

[57] ABSTRACT

Compounds of the formula:

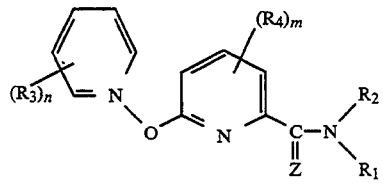

wherein $R_1$ and $R_2$ each independently represents hydrogen, optionally substituted alkyl, aryl, alkenyl, alkynyl, cycloalkyl, cycloalkylalkyl, aralkyl, alkaryl, hydroxy, alkoxy, alkenyloxy, alkynyloxy, alkylcarbonyl, alkoxycarbonyl, amino, mono- or dialkylamino, alkoxycarbonylamino, optionally substituted heterocycle or arylamino, dialkylcarbamoyl, trialkylsilyl or fused ring structure, or together form an alkenylene chain or an alkylene chain which is optionally interrupted by oxygen or sulphur or —NR—, R being hydrogen or alkyl; $R_3$ represents hydrogen or halogen, or optionally substituted alkyl, alkoxy, aryl or aryloxy, or cyano, carboxy, alkoxycarbonyl, (alkylthio) carbonyl, alkylcarbonyl, amido, alkylamido, nitro, alkenyloxy, alkynloxy, alkylthio, haloalkylthio, alkenylthio, alkynylthio, alkylsulphinyl, alkylsulphonyl, alkyloximinoalkyl or alkenyloximinoalkyl; $R_4$ represents halogen, alkyl or haloalkyl; Z represents oxygen or sulphur; m is 0–3; and n is 1–4, and certain intermediates in their production, exhibit herbicidal activity.

12 Claims, No Drawings

HERBICIDAL PICOLINAMIDE DERIVATIVES

The present invention relates to certain new picolinamide derivatives, their preparation, herbicidal compositions containing them, and their use in combating undesired plant growth.

In accordance with the present invention there is provided a compound of the general formula:

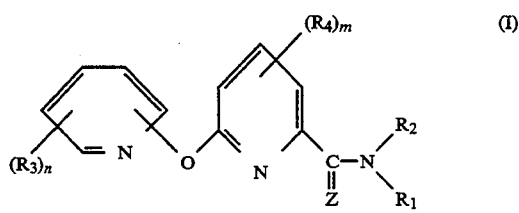

wherein $R_1$ and $R_2$ each independently represents a hydrogen atom, or an alkyl, aryl, alkenyl, alkynyl, cycloalkyl, cycloalkylalkyl, aralkyl, alkaryl, hydroxy, alkoxy, alkenyloxy, alkynyloxy, alkylcarbonyl, alkoxycarbonyl, amino, mono- or di-alkylamino, alkoxycarbonylamino group, in which groups any alkyl, alkenyl, alkynyl, cycloalkyl or aryl moiety is optionally substituted, an optionally substituted heterocyclic group, an arylamino group optionally substituted by a halogen atom, a dialkylcarbamoyl group, a trialkylsilyl group or a fused ring structure, or together form an alkenylene chain or an optionally substituted alkylene chain which is optionally interrupted by an oxygen or sulphur atom or by a group —NR— in which R represents a hydrogen atom or an alkyl group; $R_3$ represents a hydrogen or halogen atom, or an alkyl, alkoxy, aryl or aryloxy group optionally substituted by one or more of the same or different substituents selected from halogen atoms and cyano, hydroxy and alkoxy groups, or represents a cyano, carboxy, alkoxycarbonyl, (alkylthio)carbonyl, alkylcarbonyl, amido, alkylamido, nitro, alkenyloxy, alkynyloxy, alkylthio, haloalkylthio, alkenylthio, alkynylthio, alkylsulphinyl, alkylsulphonyl, alkyloximinoalkyl or alkenyloximinoalkyl group; $R_4$ represents a halogen atom or an alkyl or haloalkyl group; Z represents an oxygen or sulphur atom; m is 0–3; and n is 1–4.

Where substituted, any of the alkyl, alkenyl, alkynyl, cycloalkyl or aryl moieties in $R_1$ and $R_2$ may be substituted by one or more of the same or different substituents selected from halogen atoms and hydroxy, cyano, alkyl, alkoxy, alkylthio, alkoxycarbonyl, aryl, aryloxy, and mono- or di-alkylamino groups.

When any of the substituents $R_1$, $R_2$, $R_3$ and $R_4$ represents or contains an alkyl, alkenyl or alkynyl substituent group, this may be linear or branched and suitably has up to 12, preferably up to 6, carbon atoms. Preferred alkyl groups are methyl, ethyl, n-propyl, i-propyl, n-butyl, i-butyl, s-butyl and t-butyl. Where a cycloalkyl substituent group is present, this suitably has from 3 to 6 carbon ring atoms. An aryl group is suitably a phenyl group. An alkenylene or alkylene chain suitably has 3 to 6 chain members. A halogen atom suitably denotes a fluorine, chlorine or bromine atom; preferred haloalkyl groups are fluoroethyl, chloroethyl, trifluoromethyl and trifluoroethyl groups.

The substituent(s) $R_3$ may be at any free position or combination of positions on the pyridyloxy ring.

Each substituent $R_3$ is preferably a hydrogen, chlorine or bromine atom, or a methyl or trifluoromethyl group.

Preferably m is 0 and n is 1–2.

Preferably Z represents an oxygen atom.

The substituents $R_1$ and $R_2$ when individually present may be the same or different. Preferably $R_1$ represents an unsubstituted $C_{1-6}$ alkyl group, a $C_{1-5}$ alkyl group substituted by an alkoxy, aryloxy or cyano group or by one or more halogen atoms, for example a trifluoroethyl group, a $C_{1-6}$ alkoxy group optionally aryl-substituted, a $C_{2-7}$ alkynyl group, a $C_{2-6}$ alkenyl group, a $C_{2-6}$ alkenyloxy group, an unsubstituted aryl group, especially a phenyl group, a substituted aryl group, especially a phenyl group substituted by one or more halogen atoms, an aralkyl group, especially a benzyl or phenethyl group, an alkaryl group, especially a tolyl group, a cycloalkyl group, especially a cyclopropyl or cyclopentyl group, a substituted cycloalkylalkyl group, a heterocyclic group, especially a furfuryl or substituted isoxazolyl group, a dialkylaminoalkyl group, a naphthyl group or a trimethylsilyl group, while $R_2$ represents a hydrogen atom or an optionally substituted $C_{1-6}$ alkyl group, especially a methyl, ethyl, n-propyl, i-propyl, i-butyl or cyanomethyl group, and $R_3$ represents a hydrogen or halogen atom or a $C_{1-6}$ alkyl or $C_{1-6}$ haloalkyl group.

Particularly preferred are compounds in which $R_1$ represents a methyl, ethyl, n-propyl, i-propyl, dimethylpropyl, n-butyl, i-butyl, s-butyl, t-butyl, methoxy, ethoxy, t-butoxy, methoxyethyl, cyanomethyl, fluoroethyl, chloroethyl, trifluoroethyl, allyl, allyloxy, dimethylaminoethyl, propargyl, dimethylpropargyl, diethylpropargyl, phenethyl, pivalyl, furfuryl, naphthyl, methylphenoxyethyl, trimethylsilyl, t-butyl-isoxazolyl, cyclopropyl, cyclopentyl, unsubstituted or monofluoro-, difluoro- or monochloro-substituted phenyl, benzyl, fluorobenzyl, benzyloxy, tolyl, or dichloro-substituted cyclopropylmethyl group, $R_2$ represents a hydrogen atom or a methyl, ethyl, n-propyl, i-propyl, i-butyl or cyanomethyl group, and $R_3$ represents a hydrogen, chlorine or bromine atom or a methyl or trifluoromethyl group.

When $R_1$ and $R_2$ together represent an alkylene chain, suitably the chain consists of 4 or 5 chain atoms, and is for example a group —(CH$_2$)$_4$—, —(CH$_2$)$_5$—, —CH(CH$_3$)—(CH$_2$)$_4$—, —CH$_2$—CH(CH$_3$)—(CH$_2$)$_3$—, —(CH$_2$)$_2$CH(CH$_3$)—(CH$_2$)$_2$—, —(CH$_2$)$_2$O(CH$_2$)$_2$— or (CH$_2$)$_2$NR(CH$_2$)$_2$— in which R is a $C_{1-2}$ alkyl group, suitably methyl. When $R_1$ and $R_2$ together represent an alkenylene chain, suitably the chain consists of 4 or 5 chain atoms, and is for example a group —(CH$_2$)$_2$—CH=CH—CH$_2$—.

In accordance with the present invention there is also provided a process for the preparation of a compound of the general formula I, in which Z represents an oxygen atom, which comprises either (A) reacting a compound of the general formula:

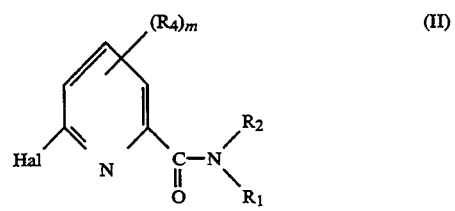

with a compound of the general formula:

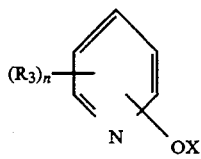

(III)

or (B) by converting a compound of the general formula:

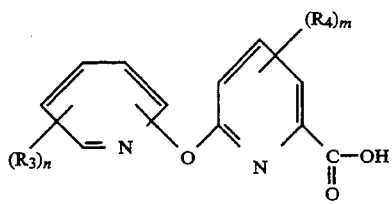

(IV)

into a derivative of the general formula:

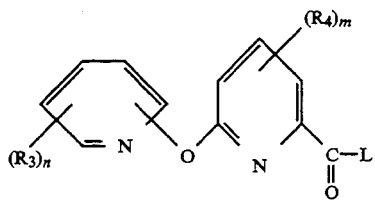

(V)

which is then reacted with an amine of the general formula $NHR_1R_2$, wherein $R_1$, $R_2$, $R_3$, $R_4$, m and n are as defined above, Hal represents a halogen atom, X represents a hydrogen atom or an alkali metal atom, and L is a leaving group, with the optional further step of converting the resultant compound of the general formula I into a further compound of the general formula I.

A leaving group is any group that will, under the reaction conditions, cleave from the starting material thus promoting reaction at a specific site.

The leaving group L may suitably be a halogen atom, for example a bromine or, especially, a chlorine atom, an alkoxy group, suitably $C_{1-4}$ alkoxy, especially methoxy, or an imidazole group.

The conversion of a resultant compound of the general formula I into a further compound of the general formula I may suitably be such as to replace a group of $R_1$ and/or $R_2$ by a different group. For example, when $R_1$ and/or $R_2$ represents a hydrogen atom it may be replaced by an alkyl group, suitably by reaction with an alkyl halide.

Suitably, Hal represents a bromine atom or, especially, a chlorine atom. Suitably, X represents a hydrogen atom.

When X represents an alkali metal atom, it is suitably a potassium or, especially, a sodium atom.

The process is suitably carried out in the presence of an inert organic solvent, for example dimethylformamide or dimethylsulphoxide, or an aromatic hydrocarbon, for example benzene or toluene, or a halogenated hydrocarbon, for example dichloromethane, or an ether, for example diethyl ether, or an ester, for example ethyl acetate.

The process is suitably carried out at a temperature in the range of 0 to 100° C, preferably at the reflux temperature of the reaction mixture, and suitably in the presence of a base, for example potassium hydroxide, and a copper catalyst, such as cuprous chloride.

Suitably, the reaction is carried out using substantially equimolar amounts of the reactants. However, it can be expedient to use one reactant in excess.

Compounds of the general formula I wherein Z represents a sulphur atom are suitably prepared by reaction of a compound of the general formula I wherein Z represents an oxygen atom, with phosphorous pentasulphide under standard conditions, for example by heating, suitably under reflux, in the presence of an inert aromatic solvent, for example benzene, toluene, pyridine or quinoline.

The compounds of the present invention may be isolated and purified by conventional techniques, for example by solvent extraction, evaporation followed by recrystallisation or by chromatography on silica.

The compounds of formula III are either known or can be prepared by conventional techniques.

When X represents an alkali metal atom, the process of method (A) may be carried out by preparation of the alkali metal pyridinolate from the corresponding pyridinol using an alkali metal alkoxide, such as sodium methoxide, followed by treatment of the pyridinolate with a substantially equimolar amount of compound II, suitably at an elevated temperature, for example under reflux, with a copper catalyst, such as cuprous chloride, in pyridine in the presence of an aromatic hydrocarbon, such as xylene, as is described in GB-A-2050168, or in dimethylformamide or dimethylsulphoxide.

Compounds of general formula II may suitably be prepared by reacting an amine of general formula $NHR_1R_2$, in which $R_1$ and $R_2$ are as defined above, with a 2-halo-6-pyridine carboxylic acid derivative of the general formula:

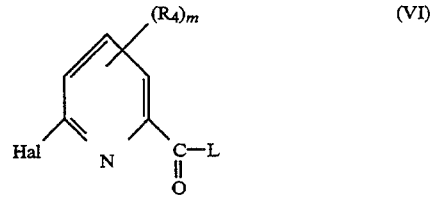

(VI)

in which $R_4$, m and Hal are as defined above and L is a leaving group. The leaving group L is as defined above.

This reaction is suitably carried out in the presence of an inert organic solvent, for example dimethylformamide or acetonitrile, or an aromatic hydrocarbon, for example benzene or toluene, or a halogenated hydrocarbon, for example dichloromethane or an ether, for example diethyl ether, or an ester, for example ethyl acetate; suitably at a temperature in the range of from 0° to 100° C. Suitably, this reaction is carried out using substantially equimolar amounts of the reactants. However, it can be expedient to use one reactant in excess, conveniently the amine.

Compounds of formula VI may be prepared from corresponding substituted picolinic acids by standard methods for the preparation of, for example, esters, using, for example, alcohols and acid catalysts or thionyl chloride, or of acid chlorides and acid bromides, using, for example, thionyl chloride or thionyl bromide, or of imidazole derivatives, using, for example, carbonyl diimidazole. The acid compounds themselves can be prepared by standard methods from chloropicolinic acid or ester thereof. Chloropicolinic acid, or ester thereof, may be prepared by the methods described in J. Pharm. Belg. (1980), 35 1, 5-11.

The substituted amines NHR$_1$R$_2$ are either known or can be prepared by conventional techniques.

The conversion of a compound of the general formula IV into a compound of the general formula V can be carried out by standard methods for the preparation of, for example, esters, using, for example, alcohols and acid catalysts or thionyl chloride, or of acid chlorides and acid bromides, using, for example, thionyl chloride or thionyl bromide, or of imidazole derivatives, using, for example, carbonyl diimidazole.

Compounds of the general formula IV may suitably be prepared by hydrolysis of compounds of the general formula:

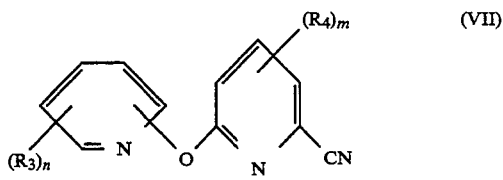

(VII)

in which R$_3$, R$_4$, m and n are as defined above.

This reaction is suitably carried out in the presence of an inert solvent such as water or ethylene glycol, using as reactants acids such as hydrochloric acid, sulphuric acid and phosphoric acid or bases such as potassium hydroxide and sodium hydroxide, at a temperature in the range 0°–150° C.

Compounds of the general formula VII, which form a further aspect of the present invention, may suitably be preparedby reacting a compound of the general formula:

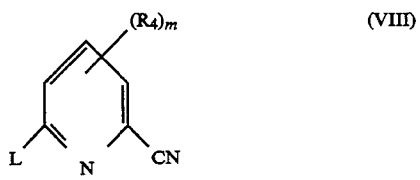

(VIII)

in which R$_4$, m and L are as defined above, with a compound of the general formula III which is also defined above. The conditions of such reaction are as for the reaction between compounds of the general formulae III and II described above.

Compounds of the general formula VIII are either known or can be prepared by conventional techniques, such as, for example, described in T. Sakamoto et al., Chem. Pharm. Bull., 33 (1985), 565–571, or in Björn Elman, Tetrahedron, 41 (1985), 4941–4948.

The compounds of general formula I have been found to have useful herbicidal activity. Also, compounds of general formula VII have been found to have some herbicidal activity. Accordingly, the present invention further provides a herbicidal composition comprising a compound of formula I or formula VII as defined above in association with at least one carrier, and a method of making such a composition is also provided which comprises bringing a compound of formula I or formula VII into association with at least one carrier.

A carrier in a composition according to the invention is any material with which the active ingredient is formulated to facilitate application to the locus to be treated, which may for example be a plant, seed or soil, or to facilitate storage, transport or handling. A carrier may be a solid or a liquid, including a material which is normally gaseous but which has been compressed to form a liquid, and any of the carriers normally used in formulating herbicidal compositions may be used. Preferably compositions according to the invention contain 0.5 to 95% by weight of active ingredient.

Suitable solid carriers include natural and synthetic clays and silicates, for example natural silicas such as diatomaceous earths; magnesium silicates, for example talcs; magnesium aluminium silicates, for example attapulgites and vermiculites; aluminium silicates, for example kaolinites, montmorillonites and micas; calcium carbonate; calcium sulphate; ammonium sulphate; synthetic hydrated silicon oxides and synthetic calcium or aluminium silicates; elements, for example carbon and sulphur; natural and synthetic resins, for example coumarone resins, polyvinyl chloride, and styrene polymers and copolymers; solid polychlorophenols; bitumen; waxes; and solid fertilisers, for example superphosphates.

Suitable liquid carriers include water; alcohols, for example isopropanol and glycols; ketones, for example acetone, methyl ethyl ketone, methyl isobutyl ketone and cyclohexanone; ethers; aromatic or araliphatic hydrocarbons, for example benzene, toluene and xylene; petroleum fractions, for example kerosine and light mineral oils; chlorinated hydrocarbons, for example carbon tetrachloride, perchloroethylene and trichloroethane. Mixtures of different liquids are often suitable.

Agricultural compositions are often formulated and transported in a concentrated form which is subsequently diluted by the user before application. The presence of small amounts of a carrier which is a surface-active agent facilitates this process of dilution. Thus preferably at least one carrier in a composition according to the invention is a surface-active agent. For example the composition may contain at least two carriers, at least one of which is a surface-active agent.

A surface-active agent may be an emulsifying agent, a dispersing agent or a wetting agent; it may be nonionic or ionic. Examples of suitable surface-active agents include the sodium or calcium salts of polyacrylic acids and lignin sulphonic acids; the condensation of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohol or alkyl phenols, for example p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of sulphonated castor oil, and sodium alkylaryl sulphonates such as dodecylbenzene sulphonate; and polymers of ethylene oxide and copolymers of ethylene oxide and propylene oxide.

The compositions of the invention may for example be formulated as wettable powders, dusts, granules, solutions, emulsifiable concentrates, emulsions, suspension concentrates and aerosols. Wettable powders usually contain 25, 50 or 75% w of active ingredient and usually contain in addition to solid inert carrier, 3–10% w of a dispersing agent and, where necessary, 0–10% w of stabiliser(s) and/or other additives such as penetrants or stickers. Dusts are usually formulated as a dust concentrate having a similar composition to that of a wettable powder but without a dispersant, and are diluted in the field with further solid carrier to give a composition usually containing ½–10% w of active ingredient. Granules are usually prepared to have a size between 10 and 100 BS mesh (1.676–0.152 mm), and may be manufactured by agglomeration or impregnation techniques. Generally, granules will contain ½–75% w active ingredient and 0–10% w of additives such as stabilisers, surfactants, slow release modifiers and binding agents. The so-called "dry-flowable powders" consist of relatively small granules having a relatively high concentration of active ingredient. Emulsifiable concentrates usually contain, in addition to a solvent and, when necessary, co-solvent, 10–50% w/v active ingredient, 2–20% w/v emulsifiers and 0–20% w/v of other additives such as stabilisers, penetrants and corrosion inhibitors. Suspension concentrates are usually compounded so as to obtain a stable, non-sedimenting flowable product and usually contain 10–75% w active ingredient, 0.5–15% w of dispersing agents, 0.1–10% w of suspending agents such as protective colloids and thixotropic agents, 0–10% w of other additives such as defoamers, corrosion inhibitors, stabilisers, penetrants and stickers, and water or an organic liquid in which the active ingredient is substantially insoluble; certain organic solids or inorganic salts may be present dissolved in the formulation to assist in preventing sedimentation or as antifreeze agents for water.

Aqueous dispersions and emulsions, for example compositions obtained by diluting a wettable powder or a concentrate according to the invention with water, also lie within the scope of the invention. The said emulsions may be of the water-in-oil or of the oil-in-water type, and may have a thick 'mayonnaise'-like consistency.

The composition of the invention may also contain other active ingredients, for example compounds possessing insecticidal or fungicidal properties or other herbicides.

The present invention still further provides the use as a herbicide of a compound of the general formula I as defined above or a composition as defined above and a method of combating undesired plant growth at a locus with such a compound or composition according to the present invention. The locus may, for example, be the soil or plants in a crop area. The dosage of active ingredient used, may, for example, be in the range of from 0.01 to 10 kg/ha, suitably 0.05 to 4 kg/ha.

Examples 1–119 below illustrate the process of method (A) of the invention; Examples 1 to 11 illustrate the preparation of intermediates of general formula II, while Examples 12 to 119 illustrate the preparation of compounds of general formula I.

EXAMPLE 1

Preparation of N-(4-fluorophenyl)-2-chloro-6-pyridinecarboxamide 6-chloropicolinic acid (51.2 g, 0.325 mol) in thionyl chloride (90 ml) was stirred and heated to reflux for 2 hours. The excess thionyl chloride was evaporated in vacuo and diethylether (250 ml) added to the residual 6-chloropicolinoyl chloride. A solution of 4-fluoroaniline (37.5 g, 0.338 mol) in diethylether (100 ml) was added with stirring, maintaining the temperature below 20° C. After the addition, the reaction mixture was stirred overnight at ambient temperature. Water was added to the reaction mixture and the organic layer separated. After a further washing with water and drying with anhydrous magnesium sulphate, the solvent was removed in vacuo to give the title compound as a pale brown solid (66 g, 82%), mp 98° C.

EXAMPLES 2 TO 11

By methods analogous to that of Example 1, further compounds of the general formula II were prepared by reaction of compounds of the general formula $NHR_1R_2$ with compounds of general formula IV. Details are given in Table I.

TABLE I

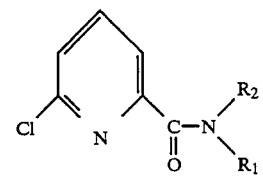

| Example No. | $R_1$ | $R_2$ | mp (°C.) | Yield (%) |
|---|---|---|---|---|
| 2 | phenyl | H | 90 | 87 |
| 3 | 2,4-$F_2$-phenyl | H | 102 | 69 |
| 4 | 2-F-phenyl | H | 88 | 91 |
| 5 | 3-F-phenyl | H | 105 | 54 |
| 6 | 4-Cl-phenyl | H | 111 | 84 |
| 7 | benzyl | H | 77 | 71 |
| 8 | 2,2,2-trifluoroethyl | H | 82 | 95 |
| 9 | n-propyl | H | 65 | 60 |
| 10 | cyclopropyl | H | 77 | 71 |
| 11 | n-propyl | n-propyl | oil | 85 |

Elemental analysis data for the intermediates of general formula II described above is set out in Table II below.

TABLE II

| Example No | Analysis (%) | | | | | |
|---|---|---|---|---|---|---|
| | C | | H | | N | |
| | Calc. | Found | Calc. | Found | Calc. | Found |
| 1 | 57.5 | 7.6 | 3.2 | 3.4 | 11.2 | 11.2 |
| 2 | 62.0 | 62.1 | 3.9 | 4.1 | 12.0 | 12.1 |
| 3 | 53.6 | 53.6 | 2.6 | 2.9 | 10.4 | 10.4 |
| 4 | 57.5 | 57.3 | 3.2 | 3.5 | 11.2 | 11.1 |
| 5 | 57.5 | 57.3 | 3.2 | 3.5 | 11.2 | 11.1 |
| 6 | 54.0 | 53.7 | 3.0 | 3.0 | 10.5 | 10.8 |
| 7 | 63.3 | 62.8 | 4.5 | 4.9 | 11.4 | 11.4 |
| 8 | 40.3 | 40.6 | 2.5 | 2.8 | 11.7 | 11.6 |
| 9 | 54.4 | 54.6 | 5.6 | 5.5 | 14.1 | 13.9 |
| 10 | 55.0 | 54.1 | 4.6 | 5.0 | 14.3 | 14.1 |
| 11 | 59.9 | 60.2 | 7.1 | 7.3 | 11.6 | 11.5 |

EXAMPLE 12

Preparation of N-(4-fluorophenyl)-2-(2'-chloro-4'-pyridyloxy)-6-pyridinecarboxamide 2-chloro-4-pyridinol (1.3 g, 10 mmol) was added to a solution of potassium hydroxide (0.56 g) in methanol (20 ml). The solvent was evaporated in vacuo after toluene (50 ml) was added to give the anhydrous potassium pyridoxylate. The residue was resolved in anhydrous N,N-dimethylformamide (7 ml). After the addition of N-(4-fluorophenyl)-2-chloro-6-pyridinecarboxamide (2.5 g, 10 mmol) and cuprous chloride (0.1 g) the mixture was heated to reflux for 10 hours. After cooling, the mixture was poured into water (150 ml) and ethyl acetate (100 ml). The organic layer was separated and the aqueous phase extracted one more time with ethyl acetate (50 ml). The combined extracts were dried with anhydrous magnesium sulphate and the solvent removed in vacuo. The residue was purified by flash silica gel column chromatography using hexane/ethyl acetate (7:3). The title compound was obtained as a pale yellow solid (1.8 g, 52%), mp 102° C.

EXAMPLES 13 TO 52

By methods analogous to that of Example 12, further compounds of the general formula I were prepared by reaction of compounds of general formula II with compounds of general formula III. Details are given in Table III.

TABLE III

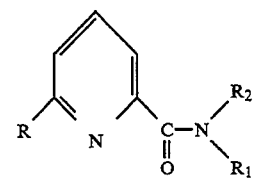

| Ex. No. | R | R₁ | R₂ | mp (°C.) | Yield (%) |
|---|---|---|---|---|---|
| 13 | 3-Cl-5-pyridyloxy | 4-F-phenyl | H | 130 | 36 |
| 14 | 2-Cl-6-pyridyloxy | 4-F-phenyl | H | 147 | 26 |
| 15 | 3-pyridyloxy | 4-F-phenyl | H | 111 | 10 |
| 16 | 3-Cl-6-pyridyloxy | 4-F-phenyl | H | 128 | 20 |
| 17 | 2-Cl-4-pyridyloxy | phenyl | H | 106 | 29 |
| 18 | 2-Cl-4-pyridyloxy | 2-F-phenyl | H | 128 | 52 |
| 19 | 2-Cl-4-pyridyloxy | 2,4-F₂-phenyl | H | 129 | 40 |
| 20 | 6-CH₃-2-pyridyloxy | 4-F-phenyl | H | 115 | 29 |
| 21 | 3-Br-5-CH₃-2-pyridyloxy | 4-F-phenyl | H | 250 | 5 |
| 22 | 3-Cl-5-pyridyloxy | 2,4-F₂-phenyl | H | 126 | 62 |
| 23 | 3-Cl-5-pyridyloxy | phenyl | H | 122 | 36 |
| 24 | 3-Cl-5-pyridyloxy | 2-F-phenyl | H | 130 | 56 |
| 25 | 3-Cl-5-pyridyloxy | n-propyl | H | 100 | 39 |
| 26 | 2-Cl-3-pyridyloxy | 4-F-phenyl | H | 150 | 29 |
| 27 | 5-CH₃-3-pyridyloxy | 4-F-phenyl | H | 102 | 46 |
| 28 | 2-Cl-4-pyridyloxy | 4-Cl-phenyl | H | 140 | 24 |
| 29 | 2-Cl-4-pyridyloxy | 4-tolyl | H | 124 | 21 |
| 30 | 2-Cl-4-pyridyloxy | benzyl | H | 110 | 10 |
| 31 | 2-Cl-4-pyridyloxy | 2,2,2-trifluoroethyl | H | 114 | 76 |
| 32 | 2-Cl-4-pyridyloxy | 3-F-phenyl | H | 105 | 30 |
| 33 | 3-Cl-5-pyridyloxy | 3-F-phenyl | H | 156 | 51 |
| 34 | 3-Cl-5-pyridyloxy | cyclopropyl | H | 102 | 14 |
| 35 | 2-Cl-6-pyridyloxy | 2,4-F₂-phenyl | H | 150 | 22 |
| 36 | 3-Cl-6-pyridyloxy | phenyl | H | 100 | 25 |
| 37 | 3-Cl-6-pyridyloxy | 2,4-F₂-phenyl | H | 168 | 37 |
| 38 | 2-CH₃-6-pyridyloxy | phenyl | H | 112 | 53 |
| 39 | 3-Cl-6-pyridyloxy | n-propyl | n-propyl | oil | 22 |
| 40 | 2-CH₃-5-pyridyloxy | benzyl | H | oil | 26 |
| 41 | 2-CH₃-6-pyridyloxy | cyclopropyl | H | oil | 10 |
| 42 | 5-CH₃-6-pyridyloxy | 4-F-phenyl | H | 169 | 55 |
| 43 | 3-Cl-5-pyridyloxy | 2,2,2-trifluoroethyl | H | 127 | 55 |
| 44 | 3-Cl-6-pyridyloxy | n-propyl | H | 181 | 17 |
| 45 | 2-CH₃-6-pyridyloxy | benzyl | H | oil | 55 |
| 46 | 2-CH₃-6-pyridyloxy | n-propyl | H | oil | 30 |
| 47 | 2-CH₃-6-pyridyloxy | 2,2,2-trifluoroethyl | H | 95 | 36 |
| 48 | 2-CH₃-4-CF₃-6-pyridyloxy | 4-F-phenyl | H | 109 | 55 |
| 49 | 2-Cl-6-pyridyloxy | phenyl | H | 112 | 41 |
| 50 | 2-CH₃-6-pyridyloxy | 2,4-F₂-phenyl | H | 105 | 28 |
| 51 | 2-CH₃-6-pyridyloxy | n-propyl | H | oil | 23 |

TABLE III-continued

| Ex. No. | R | R₁ | R₂ | mp (°C.) | Yield (%) |
|---|---|---|---|---|---|
| 52 | 3-Cl-5-pyridyloxy | benzyl | H | 105 | 20 |

EXAMPLE 53

Preparation of N-(2,4-difluorophenyl)-N-ethyl-2-(3'-chloro-5'-pyridyloxy)-6-pyridinecarboxamide Sodium hydride (0.04 g, 1.1 mmol) was added to a solution of N-(2,4-difluorophenyl)-2-(3'-chloro-5'-pyridyloxy)-6-pyridinecarboxamide (0.4 g, 1.1 mmol) in anhydrous tetrahydrofuran (10 ml). After stirring for 30 minutes, ethyl iodide (0.18 g, 1.1 mmol) was added carefully and the mixture was heated to reflux for 10 hours. After cooling, the mixture was poured into water (75 ml) and ethyl acetate (100 ml). The organic layer was separated and the aqueous phase was extracted in addition with ethyl acetate (100 ml). The combined extracts were dried with magnesium sulphate and the solvent removed in vacuo. The residue was purified by flash silica gel column chromatography using hexane/ethyl acetate (7:3). The title compound was obtained as a white solid (0.16 g, 37%), mp 84° C.

EXAMPLES 54 TO 119

By methods analogous to that of Example 53, further compounds of the general formula I were prepared by conversion of compounds of the general formula I. Details are given in Table IV.

TABLE IV

| Ex. No. | R | R₁ | R₂ | mp (°C.) | Yield (%) |
|---|---|---|---|---|---|
| 54 | 2-Cl-4-pyridyloxy | phenyl | ethyl | 93 | 12 |
| 55 | 2-Cl-4-pyridyloxy | 4-F-phenyl | ethyl | 108 | 17 |
| 56 | 2-Cl-6-pyridyloxy | 2,4-F₂-phenyl | ethyl | oil | 35 |
| 57 | 2-Cl-4-pyridyloxy | 2,4-F₂-phenyl | ethyl | 100 | 22 |
| 58 | 2-Cl-4-pyridyloxy | 2,4-F₂-phenyl | methyl | oil | 61 |
| 59 | 3-Cl-5-pyridyloxy | 4-F-phenyl | methyl | oil | 71 |
| 60 | 3-Cl-5-pyridyloxy | 4-F-phenyl | ethyl | oil | 63 |
| 61 | 2-CH₃-6-pyridyloxy | 4-F-phenyl | methyl | oil | 84 |
| 62 | 2-CH₃-6-pyridyloxy | 4-F-phenyl | ethyl | 120 | 88 |
| 63 | 2-Cl-6-pyridyloxy | 2,4-F₂-phenyl | methyl | oil | 77 |
| 64 | 3-Cl-6-pyridyloxy | 2,4-F₂-phenyl | ethyl | 110 | 75 |
| 65 | 2-CH₃-6-pyridyloxy | phenyl | methyl | 87 | 56 |
| 66 | 2-CH₃-6-pyridyloxy | phenyl | ethyl | 92 | 58 |
| 67 | 3-Cl-6-pyridyloxy | 4-F-phenyl | methyl | oil | 65 |
| 68 | 3-Cl-6-pyridyloxy | 4-F-phenyl | ethyl | 110 | 55 |

TABLE IV-continued

Structure: pyridine with R at 2-position, and at 6-position a C(=O)-N(R₁)(R₂) group

| Ex. No. | R | R₁ | R₂ | mp (°C.) | Yield (%) |
|---|---|---|---|---|---|
| 69 | 3-Cl-5-pyridyloxy | 2,2,2-trifluoroethyl | methyl | oil | 66 |
| 70 | 2-Cl-5-pyridyloxy | benzyl | methyl | oil | 72 |
| 71 | 3-Cl-6-pyridyloxy | phenyl | methyl | 121 | 57 |
| 72 | 2-Cl-4-pyridyloxy | 2,2,2-trifluoroethyl | methyl | oil | 83 |
| 73 | 5-CH₃-6-pyridyloxy | 4-F-phenyl | methyl | 155 | 77 |
| 74 | 2-CH₃-6-pyridyloxy | benzyl | methyl | oil | 64 |
| 75 | 2-Cl-4-pyridyloxy | 2,2,2-trifluoroethyl | ethyl | oil | 60 |
| 76 | 2-Cl-6-pyridyloxy | 2,2,2-trifluoroethyl | methyl | oil | 53 |
| 77 | 2-Cl-4-pyridyloxy | 2,2-Cl₂ cyclopropylmethyl | methyl | oil | 65 |
| 78 | 2-Cl-6-pyridyloxy | 2,2-Cl₂ cyclopropylmethyl | methyl | oil | 82 |
| 79 | 3-pyridyloxy | 2,2-Cl₂ cyclopropylmethyl | methyl | oil | 64 |
| 80 | 2-Cl-4-pyridyloxy | n-propyl | n-propyl | oil | 78 |
| 81 | 2-Cl-6-pyridyloxy | 4-F-phenyl | methyl | oil | 63 |
| 82 | 3-Cl-5-pyridyloxy | 2,2-Cl₂ cyclopropylmethyl | methyl | oil | 65 |
| 83 | 2-Cl-6-pyridyloxy | benzyl | methyl | oil | 77 |
| 84 | 2-Cl-4-pyridyloxy | ethyl | methyl | 45 | 82 |
| 85 | 2-Cl-4-pyridyloxy | 2-fluoroethyl | methyl | oil | 39 |
| 86 | 3-Cl-6-pyridyloxy | benzyl | methyl | oil | 94 |
| 87 | 3-Cl-6-pyridyloxy | 2,2,2-trifluoromethyl | methyl | 114 | 76 |
| 88 | 2-Cl-4-pyridyloxy | cyclopentyl | methyl | oil | 56 |
| 89 | 2-Cl-4-pyridyloxy | cyclopropyl | methyl | oil | 60 |
| 90 | 2-Cl-4-pyridyloxy | cyclopropyl | ethyl | oil | 68 |
| 91 | 2-Cl-4-pyridyloxy | 3-F-phenyl | methyl | 99 | 62 |
| 92 | 2-Cl-4-pyridyloxy | 3-F-phenyl | ethyl | oil | 53 |
| 93 | 2-Cl-4-pyridyloxy | cyanomethyl | methyl | 124 | 61 |
| 94 | 2-Cl-4-pyridyloxy | phenyl | methyl | 112 | 40 |
| 95 | 2-Cl-4-pyridyloxy | n-propyl | methyl | oil | 44 |
| 96 | 2-Cl-4-pyridyloxy | 2-methoxyethyl | methyl | oil | 60 |
| 97 | 2-Cl-4-pyridyloxy | n-propyl | ethyl | oil | 78 |
| 98 | 2-Cl-4-pyridyloxy | methoxy | methyl | oil | 74 |
| 99 | 2-Cl-4-pyridyloxy | allyl | methyl | 53 | 62 |
| 100 | 2-Cl-4-pyridyloxy | 4-F-phenyl | methyl | 101 | 48 |
| 101 | 2-Cl-4-pyridyloxy | s-butyl | methly | oil | 54 |
| 102 | 2-Cl-4-pyridyloxy | s-butyl | ethyl | oil | 46 |
| 103 | 2-Cl-4-pyridyloxy | cyclopropyl | n-propyl | oil | 53 |
| 104 | 2-Cl-4-pyridyloxy | i-propyl | methyl | oil | 95 |
| 105 | 2-Cl-4-pyridyloxy | i-propyl | ethyl | oil | 40 |
| 106 | 2-Cl-4-pyridyloxy | 4-F-benzyl | methyl | oil | 64 |
| 107 | 2-Cl-4-pyridyloxy | 4-F-benzyl | ethyl | 121 | 37 |
| 108 | 2-Cl-4-pyridyloxy | methyl | methyl | 60 | 82 |
| 109 | 2-Cl-4-pyridyloxy | n-butyl | methyl | oil | 65 |
| 110 | 2-Cl-4-pyridyloxy | n-butyl | ethyl | oil | 46 |
| 111 | 2-Cl-4-pyridyloxy | i-butyl | methyl | oil | 69 |
| 112 | 2-Cl-4-pyridyloxy | i-butyl | ethyl | oil | 42 |
| 113 | 2-Cl-4-pyridyloxy | t-butyl | methyl | oil | 55 |
| 114 | 2-Cl-4-pyridyloxy | t-butyl | ethyl | oil | 30 |
| 115 | 2-Cl-4-pyridyloxy | cyclopentyl | ethyl | 127 | 56 |
| 116 | 2-Cl-4-pyridyloxy | phenyl | i-propyl | 136 | 43 |
| 117 | 2-Cl-4-pyridyloxy | 1-phenethyl | methyl | oil | 90 |
| 118 | 2-Cl-4-pyridyloxy | 1-phenethyl | ethyl | oil | 25 |
| 119 | 2-Cl-4-pyridyloxy | pivalyl | methyl | oil | 48 |

Examples 120 to 193 below illustrate the process of method (B) of the present invention; Examples 120 to 126 illustrate the preparation of intermediate compounds of the general formula VII which are believed to be novel and form a further aspect of the present invention; Examples 127 to 132 illustrate the preparation of intermediate compounds of the general formula IV; and Examples 133 to 193 illustrate the preparation of compounds of the general formula I.

EXAMPLE 120

Preparation of 2-(2'-chloro-4'-pyridyloxy)-pyridine-6-carbonitrile 2-chloro-4-hydroxypyridine (6 g, 46.3 mmol) was added to a solution of potassium hydroxide (2.9 g, 50 mmol, 1.1 eq) in anhydrous methanol (20 ml) at ambient temperature. The solvent was evaporated in vacuo after toluene (100 ml) was added to give the dry potassium salt. The residue was resolved in anhydrous N,N-dimethylformamide (15 ml) and 6-chloro-pyridine-2-carbonitrile (6.1 g, 45 mmol) and cuprous chloride (0.3 g) was added. The reaction mixture was heated to reflux under stirring for 3 hours. After cooling, the mixture was poured into water (100 ml) and the aqueous layer extracted 3 times with ethyl acetate (100 ml). The combined extracts were dried with anhydrous magnesium sulphate and the solvent was removed in vacuo. The residue was purified by flash silica gel column chromatography using hexane/ethyl acetate (1:1). The title compound was obtained as white crystals (7.3 g, 70%), mp 121° C.

EXAMPLES 121 TO 126

By methods analogous to that of Example 120, further compounds of the general formula VII were prepared by reaction of compounds of the general formula III with compounds of the general formula VIII. Details are given in Table V.

TABLE V

Structure: pyridine with R at 2-position and CN at 6-position

| Example No. | R | mp (°C.) | Yield (%) |
|---|---|---|---|
| 121 | 3-Cl-6-pyridyloxy | 173 | 39 |
| 122 | 3-Cl-5-pyridyloxy | 87 | 66 |
| 123 | 2-CH₃-5-pyridyloxy | 103 | 60 |
| 124 | 3-CF₃-6-pyridyloxy | 119 | 15 |
| 125 | 3-pyridyloxy | 104 | 34 |
| 126 | 2-Cl-6-pyridyloxy | 143 | 24 |

EXAMPLE 127

Preparation of 2-(2'-chloro-4'-pyridyloxy)-pyridine-6-carboxylic acid 2-(2'-chloro-4'-pyridyloxy)-pyridine-6-carbonitrile (7.3 g, 31.5 mmol) (from Example 120) was suspended in concentrated hydrochloric acid (10 ml) and heated to reflux for 40 minutes. After cooling, water was added and the mixture was diluted with a 40% aqueous solution of potassium hydroxide until the mixture became clear. The solution was extracted with ethyl acetate. The aqueous layer was then acidified with dilute sulphuric acid to precipitate the title compound as a white solid (5.6 g, 72%), mp 185° C.

EXAMPLES 128 TO 132

By methods analogous to that of Example 127, further compounds of the general formula IV were prepared by hydrolysis of compounds of the general formula VII. Details are given in Table VI.

TABLE VI

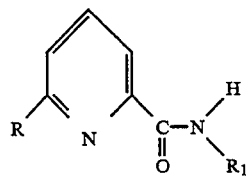

| Example No. | R | mp (°C.) | Yield (%) |
|---|---|---|---|
| 128 | 3-Cl-6-pyridyloxy | 201 | 86 |
| 129 | 3-Cl-5-pyridyloxy | 250 | 98 |
| 130 | 3-pyridyloxy | 210 | 91 |
| 131 | 3-CF$_3$-6-pyridyloxy | 270 | 78 |
| 132 | 2-Cl-6-pyridyloxy | 172 | 84 |

EXAMPLE 133

Preparation of N-(2',2'-dichlorocyclopropyl)-methyl-2-(2'-chloro-4'-pyridyloxy)-6-pyridinecarboxamide 2-(2,-chloro-4,-pyridyloxy)-pyridine-6-carboxylic acid (1 g, 4 mmol) (from Example 127) in thionyl chloride was heated to reflux for 30 minutes. The excess thionyl chloride was evaporated in vacuo and acetonitrile (5 ml) was added to the residue. A solution of (2',2'-dichlorocyclopropyl)-methylamine (0.6 g, 4.4 mmol) and triethylamine (1.5 ml) in acetonitrile (5 ml) was added with stirring at ambient temperature and the mixture was left overnight. The solvent was evaporated in vacuo and the residue resolved in ethyl acetate (25 ml). After extracting with dilute aqueous potassium hydroxide, the organic layer was dried with anhydrous magnesium sulphate. The solvent was removed in vacuo and the crude product purified by flash silica gel column chromatography using hexane/ethyl acetate (1:1). The title compound was obtained as a pale yellow solid (0.63 g, 50%), mp 106° C.

EXAMPLES 134 TO 174

By methods analogous to that of Example 133, further compounds of the general formula I were prepared by conversion of compounds of the general formula IV into compounds of the general formula V and then reaction with compounds of the general formula NHR$_1$R$_2$. Details are given in Table VII.

TABLE VII

| Ex. No. | R | R$_1$ | mp (°C.) | Yield (%) |
|---|---|---|---|---|
| 134 | 3-CF$_3$-6-pyridyloxy | 2,2,2-trifluoroethyl | 157 | 39 |
| 135 | 3-Cl-5-pyridyloxy | 2-fluoroethyl | 105 | 68 |
| 136 | 2-Cl-4-pyridyloxy | cyclopropyl | oil | 72 |
| 137 | 2-Cl-4-pyridyloxy | 2-chloroethyl | oil | 75 |
| 138 | 2-Cl-6-pyridyloxy | 2,2-Cl$_2$-cyclopropylmethyl | oil | 58 |
| 139 | 2-Cl-6-pyridyloxy | 3-F-phenyl | 88 | 58 |
| 140 | 2-Cl-6-pyridyloxy | benzyl | oil | 73 |
| 141 | 2-Cl-4-pyridyloxy | trimethylsilyl | oil | 26 |
| 142 | 2-Cl-4-pyridyloxy | 2-fluoroethyl | oil | 14 |
| 143 | 3-Cl-6-pyridyloxy | 3-F-phenyl | 202 | 56 |
| 144 | 3-Cl-6-pyridyloxy | benzyl | 176 | 65 |
| 145 | 2-Cl-4-pyridyloxy | cyclopentyl | oil | 51 |
| 146 | 2-Cl-4-pyridyloxy | cyanomethyl | 137 | 56 |
| 147 | 2-Cl-4-pyridyloxy | 2-methoxyethyl | oil | 66 |
| 148 | 2-Cl-4-pyridyloxy | 1-methyl-2-phenoxyethyl | oil | 70 |
| 149 | 2-Cl-4-pyridyloxy | propargyl | 103 | 59 |
| 150 | 2-Cl-4-pyridyloxy | allyloxy | 100 | 44 |
| 151 | 2-Cl-4-pyridyloxy | allyl | 76 | 70 |
| 152 | 2-Cl-4-pyridyloxy | ethoxy | 112 | 82 |
| 153 | 2-Cl-4-pyridyloxy | 2-naphthyl | 125 | 50 |
| 154 | 2-Cl-4-pyridyloxy | 1-naphthyl | 181 | 36 |
| 155 | 2-Cl-4-pyridyloxy | methyl | 154 | 68 |
| 156 | 2-Cl-4-pyridyloxy | s-butyl | 72 | 68 |
| 157 | 2-Cl-4-pyridyloxy | i-propyl | oil | 51 |
| 158 | 2-Cl-4-pyridyloxy | 1,1-dimethyl propargyl | 87 | 40 |
| 159 | 2-Cl-4-pyridyloxy | 4-F-benzyl | 98 | 40 |
| 160 | 2-Cl-4-pyridyloxy | ethyl | 91 | 32 |
| 161 | 2-Cl-4-pyridyloxy | n-butyl | oil | 49 |
| 162 | 2-Cl-4-pyridyloxy | i-butyl | oil | 39 |
| 163 | 2-Cl-4-pyridyloxy | t-butyl | 70 | 48 |
| 164 | 2-Cl-4-pyridyloxy | 1,1-diethyl propargyl | oil | 70 |
| 165 | 2-Cl-4-pyridyloxy | 1,1-dimethyl propyl | oil | 67 |
| 166 | 2-Cl-4-pyridyloxy | furfuryl | 66 | 61 |
| 167 | 2-Cl-4-pyridyloxy | 1-phenethyl | 97 | 51 |
| 168 | 2-Cl-4-pyridyloxy | 3-t-butyl-isoxazol-5-yl | 108 | 13 |
| 169 | 2-Cl-4-pyridyloxy | benzyloxy | 122 | 37 |
| 170 | 2-Cl-4-pyridyloxy | t-butoxy | 136 | 31 |
| 171 | 2-Cl-4-pyridyloxy | n-propyl | 75 | 77 |
| 172 | 2-Cl-4-pyridyloxy | 3,5-F$_2$-phenyl | 153 | 13 |
| 173 | 2-Cl-4-pyridyloxy | pivalyl | oil | 36 |
| 174 | 2-Cl-4-pyridyloxy | 2-dimethylaminoethyl | oil | 17 |

EXAMPLE 175

Preparation of N-(2,2,2-trifluoroethyl)-2-(3'-pyridyloxy)-6-pyridinecarboxamide To a solution of 2-(3'-pyridyloxy)-pyridine-6-carboxylic acid (0.65 g, 3 mmol) in anhydrous tetrahydrofuran (10 ml) was added carbonyldiimidazole (0.54 g, 3.3 mmol) and stirred for 30 minutes, maintaining the temperature up to 40° C. Trifluoroethylamine (0.4 g, 4 mmol) was added and the reaction mixture heated to 50° C. After 2 hours, the solution was poured into water (50 ml) and extracted twice with ethyl acetate (100 ml). The combined extracts were dried with anhydrous magnesium sulphate and the solvent was removed in vacuo. The oily residue was heated with hexane to precipitate the title compound as a white solid (0.6 g, 67%), mp 92° C.

EXAMPLES 176 TO 192

By methods analogous to that of Example 175, further compounds of the general formula I were prepared by conversion of compounds of the general formula IV into compounds of the general formula V and then reaction with compounds of the general formula $NHR_1R_2$. Details are given in Table VIII.

TABLE VIII

| Ex. No. | R | $R_1$ | $R_2$ | mp (°C.) | Yield (%) |
|---|---|---|---|---|---|
| 176 | 3-Cl-5-pyridyloxy | benzyl | methyl | oil | 71 |
| 177 | 3-Cl-5-pyridyloxy | 2,2-Cl$_2$ cyclo-propyl-methyl | H | 108 | 69 |
| 178 | 3-Cl-5-pyridyloxy | n-propyl | n-propyl | oil | 65 |
| 179 | 3-pyridyloxy | n-propyl | n-propyl | oil | 78 |
| 180 | 3-pyridyloxy | benzyl | H | 110 | 55 |
| 181 | 3-pyridyloxy | 3-F-phenyl | H | 107 | 70 |
| 182 | 3-pyridyloxy | benzyl | methyl | oil | 63 |
| 183 | 2-Cl-6-pyridyloxy | 2,2,2-trifluoro-ethyl | H | oil | 84 |
| 184 | 3-Cl-5-pyridyloxy | morpholino | | 95 | 47 |
| 185 | 2-Cl-4-pyridyloxy | pyrrolidino | | oil | 33 |
| 186 | 2-Cl-4-pyridyloxy | piperidino | | oil | 39 |
| 187 | 2-Cl-4-pyridyloxy | 2-methylpi-peridino | | oil | 38 |
| 188 | 2-Cl-4-pyridyloxy | 3-methylpi-peridino | | oil | 30 |
| 189 | 2-Cl-4-pyridyloxy | 4-methylpi-peridino | | oil | 30 |
| 190 | 2-Cl-4-pyridyloxy | 3,4-dehydro-piperidino | | 66 | 43 |
| 191 | 2-Cl-4-pyridyloxy | cyano-methyl | cyano-methyl | 155 | 15 |
| 192 | 2-Cl-4-pyridyloxy | i-butyl | i-butyl | oil | 63 |

EXAMPLE 193

Preparation of N-methyl-N-(2,2,2-trifluoroethyl)-2-(2'-chloro-6'-pyridyloxy)-6-pyridinecarboxamide Sodium hydride (0.39 g, 1.3 mmol, 80% in a dispersion of mineral oil) was added under stirring to a solution of N-trifluoroethyl-2-(2'-chloro-6'-pyridyloxy)-6-pyridinecarboxamide (0.4 g, 1.3 mmol) in anhydrous tetrahydrofuran (5 ml) at ambient temperature. After 30 minutes, methyl iodide (0.2 g, 1.4 mmol) was added and the mixture heated to reflux for 2 hours. The reaction mixture was poured into water (50 ml) and ethyl acetate (50 ml). The aqueous layer was extracted twice with ethyl acetate and the combined extracts were dried with anhydrous magnesium sulphate. The solvent was removed in vacuo and the residue purified by flash silica gel column chromatography using hexane/ethyl acetate (1:1). The title compound was obtained as a yellow oil (53%).

Elemental analysis data for the compounds of general formula I described above is set out in Table IX below.

TABLE IX

| Example No | C Calc. | C Found | H Calc. | H Found | N Calc. | N Found |
|---|---|---|---|---|---|---|
| 12 | 59.4 | 59.7 | 3.2 | 3.4 | 12.2 | 12.2 |
| 13 | 59.4 | 59.4 | 3.2 | 3.5 | 12.2 | 11.9 |
| 14 | 59.4 | 59.6 | 3.2 | 3.4 | 12.2 | 12.1 |
| 15 | 66.0 | 66.1 | 3.9 | 4.0 | 13.6 | 13.4 |
| 16 | 59.4 | 59.6 | 3.2 | 3.3 | 12.2 | 12.1 |
| 17 | 62.7 | 63.0 | 3.7 | 3.8 | 12.9 | 12.8 |
| 18 | 62.9 | 62.2 | 3.2 | 3.4 | 12.2 | 12.1 |
| 19 | 56.5 | 56.2 | 2.8 | 2.9 | 11.6 | 11.5 |
| 20 | 66.9 | 66.9 | 4.4 | 4.5 | 13.0 | 12.8 |
| 21 | 53.8 | 53.6 | 3.3 | 3.3 | 10.5 | 10.3 |
| 22 | 56.5 | 56.4 | 2.8 | 2.9 | 11.6 | 11.6 |
| 23 | 62.7 | 63.0 | 3.7 | 3.8 | 12.6 | 12.8 |
| 24 | 59.4 | 59.5 | 3.2 | 3.3 | 12.2 | 12.2 |
| 25 | 57.6 | 58.0 | 4.8 | 4.9 | 14.4 | 14.4 |
| 26 | 59.4 | 59.4 | 3.2 | 3.3 | 12.2 | 12.1 |
| 27 | 66.9 | 67.0 | 4.4 | 4.5 | 13.0 | 12.9 |
| 28 | 56.5 | 56.6 | 3.1 | 3.3 | 11.6 | 11.5 |
| 29 | 63.4 | 63.9 | 4.1 | 4.3 | 12.3 | 12.3 |
| 30 | 63.4 | 63.7 | 4.1 | 4.4 | 12.3 | 12.5 |
| 31 | 52.7 | 52.6 | 3.1 | 3.3 | 14.2 | 14.3 |
| 32 | 59.4 | 58.7 | 3.2 | 3.4 | 12.2 | 11.9 |
| 33 | 59.4 | 59.3 | 3.2 | 3.4 | 12.2 | 12.1 |
| 34 | 57.8 | 58.3 | 4.2 | 4.4 | 14.5 | 14.5 |
| 35 | 56.5 | 56.1 | 3.0 | 3.6 | 11.7 | 12.4 |
| 36 | 62.7 | 62.8 | 3.7 | 4.0 | 12.9 | 13.1 |
| 37 | 56.4 | 56.6 | 2.8 | 3.0 | 11.6 | 11.6 |
| 38 | 70.8 | 70.6 | 5.0 | 5.2 | 13.8 | 13.8 |
| 39 | 61.0 | 60.1 | 6.0 | 6.1 | 12.5 | 12.1 |
| 40 | 70.5 | 70.5 | 5.4 | 5.6 | 13.2 | 13.2 |
| 41 | 66.9 | 67.1 | 5.6 | 5.9 | 15.6 | 15.6 |
| 42 | 66.9 | 66.7 | 4.4 | 4.4 | 13.0 | 13.1 |
| 43 | 47.1 | 47.2 | 2.7 | 2.9 | 12.7 | 12.6 |
| 44 | 57.8 | 57.7 | 4.8 | 4.9 | 14.4 | 14.4 |
| 45 | 71.5 | 71.5 | 5.4 | 5.6 | 13.2 | 13.6 |
| 46 | 66.4 | 65.9 | 6.3 | 6.2 | 15.5 | 15.2 |
| 47 | 54.0 | 54.1 | 3.9 | 4.1 | 13.5 | 13.6 |
| 48 | 58.9 | 58.8 | 3.4 | 3.6 | 10.7 | 10.7 |
| 49 | 62.7 | 62.1 | 3.7 | 4.1 | 12.9 | 12.7 |
| 50 | 63.3 | 63.3 | 3.8 | 4.2 | 12.3 | 12.3 |
| 51 | 69.0 | 69.0 | 7.4 | 7.3 | 13.4 | 13.4 |
| 52 | 63.6 | 63.8 | 4.2 | 4.2 | 12.4 | 12.5 |
| 53 | 59.6 | 59.9 | 3.6 | 4.2 | 10.8 | 11.1 |
| 54 | 64.3 | 64.7 | 4.8 | 5.0 | 11.8 | 12.0 |
| 55 | 61.2 | 61.6 | 4.3 | 4.4 | 11.3 | 11.3 |
| 56 | 58.6 | 59.8 | 3.6 | 3.9 | 10.7 | 10.2 |
| 57 | 58.6 | 58.7 | 3.6 | 3.3 | 10.8 | 10.6 |
| 58 | 57.5 | 57.9 | 3.2 | 3.7 | 11.2 | 11.0 |
| 59 | 60.4 | 60.1 | 3.7 | 3.5 | 11.8 | 11.5 |
| 60 | 61.4 | 61.5 | 4.1 | 4.2 | 11.3 | 10.6 |
| 61 | 67.7 | 66.7 | 4.8 | 5.3 | 12.5 | 12.1 |
| 62 | 68.4 | 68.2 | 5.2 | 5.4 | 12.0 | 11.8 |
| 63 | 57.5 | 58.3 | 3.2 | 3.8 | 11.2 | 11.4 |
| 64 | 58.6 | 58.8 | 3.6 | 3.3 | 10.8 | 10.7 |
| 65 | 71.5 | 71.0 | 5.4 | 5.6 | 13.2 | 13.7 |
| 66 | 72.1 | 71.5 | 5.7 | 6.5 | 12.6 | 12.9 |
| 67 | 60.4 | 60.1 | 3.7 | 3.4 | 11.8 | 11.9 |
| 68 | 61.4 | 61.4 | 4.1 | 4.1 | 11.3 | 12.0 |
| 69 | 48.6 | 48.6 | 3.2 | 3.6 | 12.2 | 11.9 |
| 70 | 64.5 | 64.7 | 4.6 | 4.9 | 11.9 | 11.4 |
| 71 | 63.6 | 63.9 | 4.2 | 4.6 | 12.4 | 12.3 |
| 72 | 48.6 | 49.0 | 3.2 | 3.4 | 12.2 | 12.1 |
| 73 | 67.6 | 68.1 | 4.8 | 5.1 | 12.5 | 12.3 |
| 74 | 72.1 | 72.7 | 5.7 | 6.1 | 12.6 | 12.6 |
| 75 | 50.1 | 49.6 | 3.6 | 3.6 | 11.7 | 12.1 |
| 76 | 48.6 | 49.0 | 3.2 | 3.2 | 12.2 | 12.4 |
| 77 | 49.7 | 49.7 | 3.6 | 3.7 | 10.9 | 11.1 |
| 78 | 49.7 | 49.4 | 3.6 | 3.7 | 10.9 | 10.8 |
| 79 | 54.6 | 54.6 | 4.3 | 4.3 | 11.9 | 12.0 |
| 80 | 61.2 | 61.0 | 6.0 | 6.1 | 12.6 | 12.8 |
| 81 | 60.4 | 60.4 | 3.7 | 3.8 | 11.8 | 11.8 |
| 82 | 49.7 | 49.7 | 3.7 | 3.7 | 10.9 | 10.8 |
| 83 | 64.5 | 64.2 | 4.6 | 4.6 | 11.9 | 11.7 |
| 84 | 57.6 | 57.7 | 4.8 | 5.0 | 14.4 | 14.3 |
| 85 | 54.3 | 54.1 | 4.2 | 4.2 | 13.6 | 13.5 |
| 86 | 64.5 | 64.6 | 4.6 | 4.4 | 11.9 | 11.7 |
| 87 | 48.7 | 48.4 | 3.2 | 3.1 | 12.1 | 12.0 |
| 88 | 61.6 | 61.8 | 5.4 | 5.2 | 12.7 | 12.7 |
| 89 | 59.3 | 59.1 | 4.6 | 4.2 | 13.8 | 13.4 |

TABLE IX-continued

| Example No | C Calc. | C Found | H Calc. | H Found | N Calc. | N Found |
|---|---|---|---|---|---|---|
| 90 | 60.5 | 60.2 | 5.0 | 5.2 | 13.2 | 13.0 |
| 91 | 60.4 | 60.4 | 3.6 | 3.6 | 11.7 | 11.8 |
| 92 | 61.4 | 61.3 | 4.0 | 3.7 | 11.3 | 11.0 |
| 93 | 55.5 | 55.1 | 3.7 | 3.7 | 18.5 | 18.2 |
| 94 | 63.6 | 63.6 | 4.1 | 4.2 | 12.4 | 12.1 |
| 95 | 59.0 | 58.7 | 5.2 | 4.9 | 13.7 | 13.6 |
| 96 | 56.0 | 56.3 | 5.0 | 5.0 | 13.1 | 13.0 |
| 97 | 60.1 | 60.0 | 5.6 | 5.3 | 13.3 | 13.2 |
| 98 | 53.2 | 53.2 | 4.1 | 4.0 | 14.3 | 14.1 |
| 99 | 59.3 | 59.4 | 4.6 | 4.4 | 13.8 | 13.6 |
| 100 | 60.4 | 60.3 | 3.6 | 3.3 | 11.7 | 11.4 |
| 101 | 60.1 | 60.0 | 5.6 | 5.6 | 13.1 | 13.1 |
| 102 | 61.2 | 61.6 | 6.0 | 6.3 | 12.6 | 12.4 |
| 103 | 61.6 | 61.5 | 5.4 | 5.1 | 12.7 | 12.3 |
| 104 | 58.9 | 58.4 | 5.2 | 5.1 | 13.7 | 13.3 |
| 105 | 60.1 | 60.0 | 5.6 | 5.5 | 13.1 | 13.0 |
| 106 | 61.4 | 61.0 | 4.0 | 3.8 | 11.3 | 11.1 |
| 107 | 62.3 | 62.2 | 4.4 | 4.6 | 10.9 | 11.0 |
| 108 | 56.2 | 56.2 | 4.3 | 4.2 | 15.1 | 15.1 |
| 109 | 60.1 | 59.9 | 5.6 | 5.5 | 13.1 | 13.0 |
| 110 | 61.2 | 61.0 | 6.0 | 6.1 | 12.6 | 12.6 |
| 111 | 60.1 | 60.0 | 5.6 | 5.2 | 13.1 | 13.2 |
| 112 | 61.2 | 61.2 | 6.0 | 6.2 | 12.6 | 12.4 |
| 113 | 60.1 | 59.8 | 5.6 | 5.4 | 13.1 | 13.1 |
| 114 | 61.2 | 61.2 | 6.0 | 6.1 | 12.6 | 12.3 |
| 115 | 62.5 | 62.3 | 5.8 | 5.6 | 12.2 | 12.1 |
| 116 | 65.3 | 65.0 | 4.9 | 4.4 | 11.4 | 11.3 |
| 117 | 65.3 | 65.2 | 4.9 | 4.7 | 11.4 | 11.4 |
| 118 | 66.1 | 66.5 | 5.2 | 5.0 | 11.0 | 10.8 |
| 119 | 61.2 | 61.0 | 6.0 | 5.6 | 12.6 | 12.3 |
| 120 | 57.0 | 57.0 | 2.6 | 2.7 | 18.1 | 17.4 |
| 121 | 57.0 | 57.1 | 2.6 | 2.7 | 18.1 | 17.5 |
| 122 | 57.0 | 56.7 | 2.6 | 2.7 | 18.1 | 17.6 |
| 123 | 68.2 | 68.2 | 4.3 | 4.1 | 19.9 | 20.1 |
| 124 | 54.4 | 54.4 | 2.3 | 2.4 | 15.8 | 15.4 |
| 125 | 67.0 | 66.8 | 3.6 | 3.6 | 21.3 | 21.5 |
| 126 | 57.0 | 57.1 | 2.6 | 2.4 | 18.1 | 17.9 |
| 127 | 52.7 | 52.3 | 2.8 | 2.7 | 11.2 | 11.2 |
| 128 | 52.7 | 53.1 | 2.8 | 3.1 | 11.2 | 11.0 |
| 129 | 52.7 | 52.3 | 2.8 | 2.9 | 11.2 | 10.9 |
| 130 | 61.2 | 61.6 | 3.7 | 3.7 | 13.0 | 13.1 |
| 131 | 50.7 | 50.3 | 2.5 | 2.7 | 9.9 | 9.6 |
| 132 | 52.7 | 52.9 | 2.8 | 3.0 | 11.2 | 10.9 |
| 133 | 48.4 | 48.0 | 3.3 | 3.4 | 11.3 | 11.1 |
| 134 | 46.0 | 46.2 | 2.5 | 2.8 | 11.5 | 11.3 |
| 135 | 52.8 | 52.8 | 3.7 | 3.7 | 14.2 | 14.1 |
| 136 | 58.1 | 58.4 | 4.1 | 4.4 | 14.5 | 14.3 |
| 137 | 50.0 | 49.7 | 3.5 | 3.5 | 13.5 | 13.7 |
| 138 | 48.4 | 48.6 | 3.2 | 3.3 | 11.3 | 11.3 |
| 139 | 59.4 | 59.5 | 3.2 | 3.4 | 12.2 | 12.1 |
| 140 | 63.6 | 63.6 | 4.1 | 4.2 | 12.4 | 12.2 |
| 141 | 52.3 | 52.0 | 5.0 | 4.7 | 13.1 | 13.0 |
| 142 | 52.8 | 52.8 | 3.7 | 3.8 | 14.2 | 14.0 |
| 143 | 59.4 | 59.3 | 3.2 | 3.4 | 12.2 | 12.0 |
| 144 | 63.6 | 63.3 | 4.1 | 4.3 | 12.4 | 12.3 |
| 145 | 60.5 | 60.5 | 5.1 | 5.1 | 13.2 | 13.1 |
| 146 | 54.1 | 53.9 | 3.1 | 3.2 | 19.4 | 19.5 |
| 147 | 54.7 | 54.7 | 4.6 | 4.7 | 13.7 | 13.8 |
| 148 | 65.3 | 65.4 | 4.9 | 5.2 | 11.4 | 11.5 |
| 149 | 58.5 | 58.7 | 3.5 | 3.4 | 14.6 | 14.5 |
| 150 | 55.0 | 54.7 | 3.9 | 3.6 | 13.7 | 13.4 |
| 151 | 58.1 | 58.1 | 4.1 | 4.2 | 14.5 | 14.5 |
| 152 | 53.2 | 53.0 | 4.1 | 4.3 | 14.3 | 14.4 |
| 153 | 67.1 | 67.0 | 3.7 | 3.7 | 11.2 | 11.4 |
| 154 | 67.1 | 66.9 | 3.7 | 3.3 | 11.2 | 11.1 |
| 155 | 54.7 | 54.5 | 3.8 | 4.2 | 16.0 | 16.0 |
| 156 | 58.9 | 58.4 | 5.3 | 5.6 | 13.7 | 13.7 |
| 157 | 57.7 | 57.5 | 4.8 | 4.7 | 14.4 | 14.3 |
| 158 | 60.9 | 60.8 | 4.4 | 4.5 | 13.3 | 13.2 |
| 159 | 60.5 | 60.5 | 3.6 | 3.5 | 11.7 | 11.7 |
| 160 | 56.3 | 56.2 | 4.3 | 4.1 | 15.1 | 15.2 |
| 161 | 58.9 | 58.7 | 5.2 | 5.2 | 13.7 | 13.9 |
| 162 | 58.9 | 58.9 | 5.2 | 5.4 | 13.7 | 13.4 |
| 163 | 58.9 | 58.9 | 5.3 | 5.6 | 13.7 | 13.6 |
| 164 | 62.9 | 62.8 | 5.3 | 5.3 | 12.2 | 12.2 |
| 165 | 60.1 | 59.9 | 5.7 | 5.9 | 13.1 | 13.0 |
| 166 | 58.3 | 58.3 | 3.7 | 3.8 | 12.7 | 12.7 |
| 167 | 64.5 | 64.2 | 4.6 | 5.0 | 11.9 | 11.5 |

TABLE IX-continued

| Example No | C Calc. | C Found | H Calc. | H Found | N Calc. | N Found |
|---|---|---|---|---|---|---|
| 168 | 58.0 | 57.7 | 4.6 | 4.5 | 15.0 | 15.0 |
| 169 | 60.8 | 60.8 | 4.0 | 4.1 | 11.8 | 11.8 |
| 170 | 56.0 | 55.9 | 5.0 | 5.1 | 13.1 | 13.0 |
| 171 | 57.6 | 57.6 | 4.8 | 5.0 | 14.4 | 14.3 |
| 172 | 55.0 | 55.0 | 2.8 | 2.9 | 11.6 | 11.2 |
| 173 | 60.1 | 60.1 | 5.7 | 5.8 | 13.1 | 13.0 |
| 174 | 56.2 | 56.0 | 5.3 | 5.1 | 17.5 | 17.4 |
| 175 | 52.5 | 51.3 | 3.4 | 3.6 | 15.1 | 15.5 |
| 176 | 64.5 | 64.5 | 4.6 | 4.7 | 11.9 | 11.6 |
| 177 | 48.4 | 47.7 | 3.3 | 3.5 | 11.3 | 11.2 |
| 178 | 61.2 | 60.5 | 6.0 | 6.2 | 12.6 | 12.3 |
| 179 | 68.2 | 67.3 | 7.1 | 7.3 | 14.0 | 14.2 |
| 180 | 70.8 | 70.8 | 5.0 | 5.2 | 13.8 | 14.1 |
| 181 | 66.0 | 66.1 | 3.9 | 4.1 | 13.6 | 13.6 |
| 182 | 71.5 | 71.2 | 5.4 | 5.5 | 13.2 | 13.2 |
| 183 | 47.1 | 46.9 | 2.7 | 2.9 | 12.7 | 12.5 |
| 184 | 56.3 | 56.4 | 4.4 | 4.4 | 13.1 | 13.1 |
| 185 | 59.3 | 59.2 | 4.6 | 4.3 | 13.8 | 13.6 |
| 186 | 60.5 | 60.2 | 5.0 | 5.3 | 13.2 | 13.1 |
| 187 | 61.4 | 61.1 | 5.4 | 5.3 | 12.6 | 12.3 |
| 188 | 61.4 | 61.3 | 5.4 | 5.0 | 12.6 | 12.2 |
| 189 | 61.4 | 61.2 | 5.4 | 5.4 | 12.6 | 12.7 |
| 190 | 60.9 | 60.8 | 4.4 | 4.5 | 13.3 | 13.3 |
| 191 | 55.0 | 55.1 | 3.1 | 3.4 | 21.4 | 21.3 |
| 192 | 63.1 | 63.1 | 6.7 | 6.8 | 11.6 | 11.1 |
| 193 | 48.6 | 49.1 | 3.2 | 3.2 | 11.2 | 12.4 |

EXAMPLE 194

Herbicidal Activity

To evaluate their herbicidal activity, compounds according to the invention were tested using as representative range of plants: maize, *Zea mays* (Mz); rice, *Oryza sativa* (R); barnyard grass, *Echinochloa crusgalli* (BG); oat, *Avena sativa* (O); linseed, *Linum usitatissimum* (L); mustard, *Sinapsis alba* (M); sugar beet, *Beta vulgaris* (SB); and soya bean, *Glycine max* (S).

The tests fall into two categories, pre-emergence and post-emergence. The pre-emergence tests involved spraying a liquid formulation of the compound onto the soil in which the seeds of the plant species mentioned above had recently been sown. The post-emergence tests involved two types of test, viz., soil drench and foliar spray tests. In the soil drench tests the soil in which the seedling plants of the above species were growing was drenched with a liquid formulation containing a compound of the invention, and in the foliar spray tests the seedling plants were sprayed with such a formulation.

The soil used in the tests was a prepared horticultural loam.

The formulations used in the tests were prepared from solutions of the test compounds in acetone containing 0.4% by weight of an alkylphenol/ethylene oxide condensate available under the trade mark TRITON X-155. These acetone solutions were diluted with water and the resulting formulations applied at dosage levels corresponding to 5 kg or 1 kg of active material per hectare in a volume equivalent to 600 liters per hectare in the soil spray and foliar spray test, and at a dosage of level equivalent to 10 kilograms of active material per hectare in a volume equivalent to approximately 3,000 liters per hectare in the soil drench tests.

In the pre-emergence tests untreated sown soil and in the post-emergence tests untreated soil bearing seedling plants were used as controls.

The herbicidal effects of the test compounds were assessed visually twelve days after spraying the foliage and the soil, and thirteen days after drenching the soil and were recorded on 0-9 scale. A rating 0 indicates growth as untreated control, a rating 9 indicates death. An increase of 1 unit on the linear scale approximates to a 10% increase in the level of effect.

The results of the tests are set out in Table X below, in which the compounds are identified by reference to the preceding Examples. Absence of a numeral in the Table indicates a zero rating; an asterisk indicates that no result was obtained.

TABLE X

| Compound of Ex. No. | Soil drench 10 kg/ha | | | | | | | | Dosage kg/ha | Foliar spray | | | | | | | | Pre-emergence | | | | | | | |
|---|---|---|---|---|---|---|---|---|---|---|---|---|---|---|---|---|---|---|---|---|---|---|---|---|---|
| | Mz | R | BG | O | L | M | SB | S | | Mz | R | BG | O | L | M | SB | S | Mz | R | BG | O | L | M | SB | S |
| 12 | 7 | 7 | 8 | 8 | 5 | 7 | 8 | 3 | 5 | 7 | 5 | 9 | 5 | 7 | 8 | 9 | 7 | 5 | 4 | 8 | 6 | 8 | 9 | 9 | 6 |
| | | | | | | | | | 1 | 5 | 2 | 8 | 4 | 7 | 8 | 8 | 7 | 2 | 2 | 6 | 5 | 4 | 6 | 8 | 2 |
| 13 | 5 | 3 | 6 | 3 | 2 | 5 | 5 | 2 | 5 | 6 | 4 | 9 | 5 | 6 | 9 | 9 | 8 | 2 | 2 | 6 | 1 | 3 | 6 | 7 | |
| | | | | | | | | | 1 | 4 | 2 | 9 | 4 | 6 | 9 | 9 | 6 | 1 | 1 | 4 | 1 | 1 | 4 | 5 | |
| 14 | 3 | | 4 | 1 | | 4 | 3 | | 5 | 2 | 1 | 8 | 3 | 6 | 8 | 9 | 6 | | | | | | 3 | 3 | |
| | | | | | | | | | 1 | 2 | | 7 | 1 | 5 | 8 | 8 | 5 | | | | | | 3 | 2 | |
| 15 | | | 5 | | | 3 | 3 | | 5 | 3 | 2 | 8 | 2 | 6 | 8 | 8 | 7 | | | 2 | | 3 | 6 | 4 | 2 |
| | | | | | | | | | 1 | 1 | 1 | 7 | 1 | 4 | 8 | 7 | 6 | | | | | 2 | | 2 | |
| 16 | 4 | 2 | 4 | 2 | 1 | 6 | 2 | 2 | 5 | 5 | 1 | 8 | 4 | 6 | 9 | 9 | 7 | 1 | | 1 | | | 2 | 1 | |
| | | | | | | | | | 1 | 2 | | 7 | 2 | 5 | 9 | 9 | 6 | | | | | 2 | | | |
| 17 | 7 | 7 | 8 | 7 | 6 | 7 | 7 | 2 | 5 | 6 | 5 | 8 | 5 | 8 | 9 | 9 | 8 | 5 | 5 | 6 | 6 | 4 | 8 | 8 | 3 |
| | | | | | | | | | 1 | 5 | 5 | 8 | 4 | 7 | 9 | 9 | 8 | 3 | | 3 | 2 | 2 | 6 | 6 | 2 |
| 18 | 6 | 6 | 7 | 6 | 5 | 5 | 6 | 4 | 5 | 5 | 5 | 8 | 7 | 7 | 9 | 9 | 7 | 3 | 1 | 6 | 1 | 2 | 7 | 4 | 1 |
| | | | | | | | | | 1 | 4 | 5 | 8 | 4 | 7 | 9 | 9 | 7 | 2 | | 2 | 1 | 1 | 4 | 2 | |
| 19 | 7 | 6 | 7 | 6 | 4 | 5 | 7 | 2 | 5 | 5 | 5 | 8 | 6 | 7 | 9 | 9 | 7 | 4 | 2 | 4 | 5 | 3 | 7 | 7 | 2 |
| | | | | | | | | | 1 | 4 | 2 | 7 | 3 | 7 | 9 | 9 | 7 | 3 | | 2 | 3 | 1 | 5 | 4 | |
| 20 | | | 4 | | 3 | 2 | | | 5 | 4 | 3 | 6 | 4 | 6 | 9 | 9 | 6 | | | | | | 4 | | |
| | | | | | | | | | 1 | 2 | 3 | 2 | 5 | 8 | 7 | 5 | | | | | | 2 | | | |
| 21 | * | * | * | * | * | * | * | * | 5 | 3 | | | | | 5 | 2 | 3 | | | | | | | | |
| | | | | | | | | | 1 | | | | | 2 | 1 | | | | | | | | | | |
| 22 | 4 | | 5 | 2 | | 1 | 3 | | 5 | 5 | 2 | 8 | 5 | 5 | 9 | 9 | 8 | 5 | 2 | 5 | | 2 | 7 | 7 | |
| | | | | | | | | | 1 | 5 | 8 | 5 | 5 | 9 | 9 | 7 | 1 | | 3 | | | 7 | 7 | | |
| 23 | 4 | 2 | 6 | | | 4 | 5 | | 5 | 5 | 4 | 8 | 5 | 6 | 9 | 9 | 7 | 3 | | 4 | 1 | 3 | 8 | 9 | |
| | | | | | | | | | 1 | 4 | 1 | 8 | 5 | 6 | 8 | 9 | 7 | 1 | | 1 | | 1 | 7 | 7 | |
| 24 | | | | | | | | | 5 | 5 | | 7 | 4 | 4 | 9 | 9 | 7 | 3 | | 2 | | 1 | 6 | 5 | |
| | | | | | | | | | 1 | 2 | | 6 | 3 | 4 | 8 | 9 | 6 | 1 | | 2 | | | 6 | 4 | |
| 25 | 6 | 2 | 3 | 2 | 4 | 6 | 5 | | 5 | 5 | 4 | | 9 | 4 | 7 | 9 | 9 | 8 | 7 | 5 | 7 | 4 | 2 | 9 | 9 | 3 |
| | | | | | | | | | 1 | 2 | | 8 | 4 | 6 | 9 | 9 | 7 | 5 | | 6 | | | 8 | 8 | |
| 26 | | | | | | | | | 5 | 3 | | 2 | 1 | 1 | 4 | 3 | 2 | | | | | | | | |
| | | | | | | | | | 1 | 1 | | | 1 | | 1 | 4 | | | | | | | | | |
| 27 | | | | | | | | | 5 | 4 | 5 | 5 | 2 | 5 | 8 | 8 | 6 | | | | | | 4 | | |
| | | | | | | | | | 1 | 2 | 3 | 1 | 3 | 7 | 6 | 4 | | | | | | 2 | | | |
| 28 | 5 | 5 | 6 | 6 | 2 | 3 | 4 | | 5 | 8 | 4 | 8 | 5 | 7 | 9 | 9 | 8 | 4 | | 5 | 2 | 2 | 5 | 6 | |
| | | | | | | | | | 1 | 5 | 2 | 7 | 3 | 7 | 9 | 9 | 7 | | | | 1 | 3 | 3 | | |
| 29 | 5 | 5 | 7 | 5 | | 4 | 6 | 1 | 5 | 8 | 5 | 8 | 7 | 7 | 8 | 9 | 7 | 4 | 2 | 5 | 3 | 2 | 6 | 4 | |
| | | | | | | | | | 1 | 6 | 4 | 7 | 3 | 6 | 8 | 9 | 7 | 2 | | 2 | 1 | 1 | 4 | 2 | |
| 30 | 6 | 5 | 6 | 5 | 3 | 6 | 8 | 4 | 5 | 6 | 4 | 8 | 4 | 7 | 9 | 9 | 8 | 3 | 4 | 5 | 2 | 2 | 8 | 8 | 7 |
| | | | | | | | | | 1 | 4 | 2 | 6 | 2 | 6 | 9 | 9 | 8 | 1 | | 4 | | | 7 | 8 | 2 |
| 31 | 9 | 9 | 8 | 7 | 8 | 9 | 9 | 8 | 5 | 8 | 7 | 9 | 7 | 8 | 9 | 9 | 8 | 9 | 9 | 9 | 9 | 9 | 9 | 9 | 9 |
| | | | | | | | | | 1 | 5 | 4 | 8 | 5 | 8 | 9 | 9 | 8 | 9 | 8 | 9 | 9 | 9 | 9 | 9 | 9 |
| 32 | 6 | 4 | 6 | 6 | 2 | 4 | 5 | | 5 | 8 | 6 | 9 | 7 | 8 | 9 | 9 | 8 | 6 | 3 | 7 | 6 | 7 | 9 | 8 | 4 |
| | | | | | | | | | 1 | 6 | 4 | 8 | 5 | 8 | 8 | 9 | 8 | 4 | 1 | 5 | 5 | 6 | 8 | 8 | |
| 33 | 2 | | 4 | 5 | 2 | 3 | * | | 5 | 6 | | 8 | 4 | 5 | 9 | 9 | 7 | 3 | | 4 | | 3 | 7 | 4 | 3 |
| | | | | | | | | | 1 | 3 | | 6 | 3 | 5 | 8 | 8 | 6 | 1 | | 1 | | 1 | 7 | 1 | 1 |
| 34 | 7 | 5 | 7 | 3 | 7 | 9 | 9 | 7 | 5 | 3 | 3 | 9 | 6 | 8 | 9 | 8 | 8 | 5 | 6 | 4 | 7 | 8 | 9 | 8 | |
| | | | | | | | | | 1 | 1 | 1 | 4 | 4 | 5 | 8 | 7 | 6 | 1 | | | | 3 | 7 | 5 | 3 |
| 35 | | | | | | | | | 5 | 2 | | 3 | | 5 | 8 | 8 | 5 | | | | | | | | |
| | | | | | | | | | 1 | 1 | | 2 | | 3 | 8 | 7 | 4 | | | | | | | | |
| 36 | 2 | 1 | 5 | | | 6 | 6 | | 5 | 4 | 3 | 7 | 3 | 6 | 9 | 9 | 6 | | | | | | 4 | | |
| | | | | | | | | | 1 | 1 | 5 | 1 | 5 | 8 | 9 | 6 | | | | | | 2 | | | |
| 37 | | | | | | | | | 5 | * | * | * | * | * | * | * | * | | | | | | 3 | | |
| | | | | | | | | | 1 | 2 | 2 | 1 | 3 | 8 | 8 | 5 | | | | | | 1 | | | |
| 38 | | | | | | | | | 5 | 4 | | 5 | 2 | 5 | 7 | 9 | 5 | | | | | | | | |
| | | | | | | | | | 1 | 2 | | 3 | | 6 | 7 | 3 | | | | | | | | | |
| 39 | * | * | * | * | * | * | * | * | 5 | 4 | | 4 | | 3 | 8 | 8 | 3 | | | | | | | | |
| | | | | | | | | | 1 | 2 | | | | | 6 | 3 | 2 | | | | | | | | |
| 40 | | | | | | | | | 5 | 2 | | 4 | | 3 | 7 | 7 | 2 | | | | | | | | |
| | | | | | | | | | 1 | | | | | | 2 | | 1 | | | | | | | | |
| 42 | | | | | | | | | 5 | 3 | | 3 | 1 | 3 | 7 | 6 | 4 | | | | | | | | |
| | | | | | | | | | 1 | 2 | | | | 1 | 4 | 2 | 2 | | | | | | | | |
| 43 | 7 | 6 | 7 | 6 | 6 | 8 | 9 | 7 | 5 | 3 | 3 | 5 | 1 | 8 | 9 | 9 | 8 | 7 | 6 | 9 | 4 | 6 | 9 | 9 | 7 |
| | | | | | | | | | 1 | 2 | | | 6 | 9 | 8 | 6 | 4 | 2 | 5 | | 2 | 8 | 9 | 2 | | |
| 44 | | | | 1 | 5 | 6 | | | 5 | | | | 2 | 4 | 3 | 3 | | | | | | 4 | 5 | 1 | | |
| | | | | | | | | | 1 | | | | | | | 2 | | | | | | 2 | | | | |
| 45 | | | | | | | | | 5 | | 2 | | 4 | 7 | 8 | 6 | | | | | | 3 | 3 | | | |
| | | | | | | | | | 1 | | | | 1 | 5 | 4 | 4 | | | | | | | | | | |
| 46 | | | 5 | | 4 | 4 | 5 | | 5 | 4 | 1 | 4 | 2 | 6 | 7 | 8 | 6 | | | 1 | | | 4 | 7 | |
| | | | | | | | | | 1 | | | | 2 | 4 | 5 | 5 | | | | | | 1 | 2 | | | |
| 47 | 4 | 3 | 6 | 3 | 4 | 6 | 6 | 6 | 5 | 4 | | 5 | | 6 | 8 | 8 | 6 | 3 | 2 | 4 | | 4 | 7 | 7 | 5 |

TABLE X-continued

| Compound of Ex. No. | Soil drench 10 kg/ha | | | | | | | | Dosage kg/ha | Foliar spray | | | | | | | | Pre-emergence | | | | | | | |
|---|---|---|---|---|---|---|---|---|---|---|---|---|---|---|---|---|---|---|---|---|---|---|---|---|---|
| | Mz | R | BG | O | L | M | SB | S | | Mz | R | BG | O | L | M | SB | S | Mz | R | BG | O | L | M | SB | S |
| 48 | | | | | | | | 1 | 1 | | 2 | | | 5 | 7 | 6 | 6 | | | | | 1 | 5 | 6 | 1 |
| | | | | | | | | | 5 | 4 | 1 | 1 | 2 | 4 | 6 | 9 | 4 | | | | | | | | |
| | | | | | | | | | 1 | 2 | | | | 2 | 3 | 6 | 2 | | | | | | | | |
| 49 | 4 | | 5 | | 2 | 3 | | | 5 | 7 | | 6 | 4 | 6 | 7 | 9 | 6 | | | 3 | | | 3 | | |
| | | | | | | | | | 1 | 4 | | 5 | 1 | 6 | 7 | 9 | 5 | | | 1 | | | 1 | | |
| 50 | | | | | | | | | 5 | 5 | | 6 | 4 | 6 | 7 | 9 | 6 | | | | | | 2 | 3 | |
| | | | | | | | | | 1 | 2 | | 4 | 1 | 5 | 7 | 9 | 6 | | | | | | 1 | 3 | |
| 51 | | | | | | | | | 5 | 3 | 2 | 3 | | | 6 | 7 | 8 | 5 | | | | | 2 | 5 | 4 | |
| | | | | | | | | | 1 | 1 | | 1 | | 3 | 5 | 4 | 2 | | | | | 1 | 5 | 3 | |
| 52 | | | | | | | | | 5 | 3 | | 3 | | 5 | 9 | 9 | 6 | | | | | | | | |
| | | | | | | | | | 1 | 2 | | 2 | | 2 | 7 | 6 | 4 | | | | | | | | |
| 53 | * | * | * | * | * | * | * | * | 5 | 7 | 3 | 7 | 3 | 6 | 9 | 9 | 7 | 7 | | 3 | | 1 | 7 | 4 | 2 |
| | | | | | | | | | 1 | 4 | | 3 | | 4 | 9 | 9 | 6 | | | | | | 4 | 3 | |
| 54 | 7 | 7 | 7 | 5 | 8 | 9 | 9 | 8 | 5 | 6 | 4 | 7 | 5 | 8 | 9 | 9 | 8 | 7 | 5 | 8 | 7 | 8 | 9 | 9 | 8 |
| | | | | | | | | | 1 | 3 | | 5 | 4 | 7 | 9 | 9 | 8 | 5 | | 7 | 5 | 6 | 9 | 9 | 7 |
| 55 | 8 | 6 | 8 | 7 | 7 | 8 | 9 | 8 | 5 | 8 | 3 | 8 | 8 | 8 | 9 | 9 | 8 | 7 | 7 | 7 | 6 | 9 | 9 | 9 | 9 |
| | | | | | | | | | 1 | 5 | | 4 | 2 | 7 | 9 | 9 | 7 | 5 | 3 | 6 | 3 | 6 | 8 | 9 | 7 |
| 56 | | | | | 7 | 4 | 2 | | 5 | * | * | * | * | * | * | * | * | * | * | * | * | * | * | * | * |
| | | | | | | | | | 1 | 3 | 2 | 2 | 2 | 4 | 8 | 8 | 5 | | | | | | 5 | | 1 |
| 57 | 6 | 4 | 7 | 6 | 5 | 8 | 8 | 6 | 5 | 7 | 4 | 9 | 6 | 7 | 9 | 9 | 8 | 6 | 2 | 6 | 5 | 6 | 9 | 9 | 7 |
| | | | | | | | | | 1 | 3 | | 7 | 4 | 7 | 9 | 9 | 6 | 3 | | 4 | 2 | 4 | 8 | 9 | 3 |
| 58 | 7 | 6 | 7 | 6 | 7 | 8 | 8 | 7 | 5 | 8 | 4 | 8 | 6 | 7 | 9 | 9 | 8 | 7 | 6 | 7 | 8 | 8 | 9 | 9 | 8 |
| | | | | | | | | | 1 | 3 | 2 | 4 | 4 | 7 | 9 | 9 | 8 | 2 | | 4 | 4 | 4 | 9 | 9 | 7 |
| 59 | 6 | 5 | 6 | 4 | 6 | 8 | 7 | 6 | 5 | 4 | 3 | 7 | 5 | 7 | 9 | 9 | 8 | 6 | 5 | 6 | 5 | 5 | 9 | 9 | 6 |
| | | | | | | | | | 1 | 2 | | 3 | 3 | 6 | 9 | 9 | 7 | 3 | | 2 | | 3 | 8 | 8 | 3 |
| 60 | 5 | * | 4 | 2 | 3 | 7 | 6 | 4 | 5 | 6 | 2 | 7 | 4 | 7 | 9 | 9 | 6 | 5 | 3 | 7 | 3 | 5 | 9 | 9 | 6 |
| | | | | | | | | | 1 | 3 | | 3 | 1 | 6 | 9 | 9 | 5 | 2 | | 3 | | 3 | 8 | 7 | |
| 61 | | | | | 1 | 6 | 2 | * | 5 | | | 2 | | 5 | 8 | 7 | 4 | | | | | | 7 | 3 | |
| | | | | | | | | | 1 | | | | | 2 | 7 | 4 | 2 | | | | | | 4 | | |
| 62 | | | | | 4 | 5 | 4 | | 5 | | | 6 | | 6 | 8 | 7 | 3 | | | | | | 7 | 3 | |
| | | | | | | | | | 1 | | | | | 3 | 5 | 2 | | | | | | | 2 | | |
| 63 | | | | | | 7 | 7 | 1 | 5 | 2 | | 2 | | 1 | 9 | 9 | 4 | | | | | | 4 | | |
| | | | | | | | | | 1 | * | * | * | * | * | * | * | * | * | * | * | * | * | * | * | |
| 64 | * | * | * | * | * | * | * | * | 5 | 2 | | 3 | 1 | 4 | 9 | 8 | 2 | | | | | | 8 | 8 | |
| | | | | | | | | | 1 | | | 1 | | 2 | 8 | 7 | | | | | | | 5 | 2 | |
| 65 | | | | | 2 | 6 | 2 | | 5 | 3 | 1 | 3 | 1 | 5 | 9 | 7 | 5 | | | | | | 6 | 2 | 5 |
| | | | | | | | | | 1 | 1 | | | | 2 | 6 | 4 | 3 | | | | | | 3 | | |
| 66 | | | | | | | | | 5 | 5 | 2 | 5 | 3 | 6 | 9 | 9 | 5 | | | | | | 6 | 2 | |
| | | | | | | | | | 1 | 2 | | 2 | | 3 | 7 | 5 | 3 | | | | | | 5 | | |
| 67 | * | * | * | * | * | * | * | * | 5 | | | 2 | | 6 | 9 | 9 | 4 | | | 2 | | | 9 | 9 | |
| | | | | | | | | | 1 | | | | | 3 | 8 | 8 | 4 | | | | | | 8 | 8 | |
| 68 | | | | | 3 | 8 | 7 | 3 | 5 | 4 | 2 | 3 | 1 | 6 | 9 | 9 | 6 | | | 2 | | 2 | 9 | 9 | |
| | | | | | | | | | 1 | 3 | | 2 | | 4 | 8 | 8 | 5 | | | | | 1 | 7 | 7 | |
| 69 | 4 | | 3 | 2 | 4 | 7 | 8 | 5 | 5 | 6 | 2 | 5 | 3 | 7 | 9 | 9 | 7 | 6 | | 8 | 2 | 2 | 7 | 9 | 6 |
| | | | | | | | | | 1 | 2 | | | | 4 | 8 | 7 | 6 | 1 | | | | 1 | 5 | 5 | |
| 70 | 7 | 6 | 7 | 6 | 6 | 7 | 7 | * | 5 | 7 | 4 | 8 | 5 | 8 | 9 | 9 | 9 | 7 | 7 | 7 | 6 | 6 | 9 | 9 | 8 |
| | | | | | | | | | 1 | 3 | | 2 | 2 | 7 | 9 | 9 | 8 | 5 | 2 | 4 | 2 | 3 | 7 | 8 | 2 |
| 71 | | | 2 | | 5 | 8 | 9 | 3 | 5 | 5 | | 4 | | 6 | 9 | 9 | 6 | | | 2 | | 2 | 9 | 8 | 2 |
| | | | | | | | | | 1 | | | | | 3 | 8 | 9 | 5 | | | | | | 7 | 5 | |
| 72 | 8 | 7 | 7 | 7 | 8 | 9 | * | 9 | 5 | * | * | * | * | * | * | * | * | * | * | * | * | * | * | * | * |
| | | | | | | | | | 1 | 2 | 1 | 4 | 2 | 7 | 9 | 9 | 8 | 6 | 7 | 5 | 6 | 5 | 9 | 9 | 7 |
| 73 | | | | | | | | | 5 | 2 | | 2 | 1 | 5 | 7 | 6 | 3 | | | | | | | | |
| | | | | | | | | | 1 | | | | | | 4 | 3 | 2 | | | | | | | | |
| 74 | | | | | | | | | 5 | | | 2 | | 5 | 6 | 4 | 2 | | | | | | | | |
| | | | | | | | | | 1 | | | | | | | | | | | | | | | | |
| 75 | * | * | * | * | * | * | * | * | 5 | 6 | 4 | 8 | 3 | 9 | 9 | 9 | 8 | 9 | 7 | 9 | 8 | 9 | 9 | 9 | 9 |
| | | | | | | | | | 1 | 4 | 2 | 5 | 1 | 8 | 9 | 9 | 8 | 3 | 2 | 5 | 4 | 5 | 9 | 9 | 7 |
| 76 | | | | | | | | | 5 | * | * | * | * | * | * | * | * | * | * | * | * | * | * | * | * |
| | | | | | | | | | 1 | 3 | | 4 | | 4 | 7 | 7 | 6 | 3 | | | | 3 | 6 | 5 | |
| 77 | * | * | * | * | * | * | * | * | 5 | * | * | * | * | * | * | * | * | * | * | * | * | * | * | * | * |
| | | | | | | | | | 1 | 5 | | 5 | 2 | 6 | 8 | 9 | 8 | 4 | 2 | 3 | | | 6 | 6 | |
| 78 | * | * | * | * | * | * | * | * | 5 | 6 | | 2 | | 2 | 7 | 8 | 6 | | | | | | | | |
| | | | | | | | | | 1 | | | | | | 6 | 6 | 5 | | | | | | | | |
| 79 | | | | | | | | | 5 | | | 7 | 4 | 2 | 8 | 7 | 7 | | | | | | | | |
| | | | | | | | | | 1 | | | | | | 3 | 3 | 6 | | | | | | | | |
| 80 | 8 | 6 | 8 | 7 | 5 | 6 | * | 7 | 5 | 7 | 1 | 8 | 6 | 7 | 8 | 9 | 8 | 6 | 3 | 8 | 3 | 2 | 7 | 8 | 1 |
| | | | | | | | | | 1 | 6 | | 8 | 4 | 6 | 8 | 9 | 8 | 3 | 2 | 7 | | 2 | 6 | 7 | |
| 81 | 5 | | 4 | | 4 | 7 | 6 | 5 | 5 | 5 | 1 | 8 | 3 | 5 | 8 | 9 | 9 | 2 | | 5 | | 5 | 9 | 8 | 5 |
| | | | | | | | | | 1 | 2 | 1 | 4 | 1 | 3 | 7 | 9 | 8 | | | | | 3 | 8 | 7 | |
| 82 | | | | | | | | | 5 | 3 | | 8 | | 3 | 9 | 9 | 8 | | | | | | | | |
| | | | | | | | | | 1 | 3 | | 3 | | 3 | 6 | 8 | 8 | | | | | | | | |
| 83 | | | | | | | | | 5 | 4 | | 7 | | | 7 | 7 | 7 | | | | | | | | |
| | | | | | | | | | 1 | 2 | | | | | 5 | 5 | 4 | | | | | | | | |
| 84 | 7 | | 6 | 3 | 6 | 7 | 8 | 7 | 5 | 2 | 2 | 4 | 3 | 4 | 7 | 7 | 7 | 4 | | 2 | | 2 | 4 | 6 | 3 |
| | | | | | | | | | 1 | | | 3 | | 6 | 5 | 6 | | | | | | | 2 | | |
| 85 | 6 | | 6 | 5 | 3 | 7 | 8 | 7 | 5 | 4 | | * | * | 5 | 7 | 7 | 8 | * | | 3 | | 4 | 6 | 7 | * |
| | | | | | | | | | 1 | * | | * | * | * | * | * | * | | | | | | | | |
| 86 | | | | | | | | | 5 | | | 4 | 2 | 4 | 7 | 7 | 4 | | | | | | | | |

TABLE X-continued

| Compound of Ex. No. | Soil drench 10 kg/ha | | | | | | | | Dosage kg/ha | Foliar spray | | | | | | | | Pre-emergence | | | | | | | |
|---|---|---|---|---|---|---|---|---|---|---|---|---|---|---|---|---|---|---|---|---|---|---|---|---|---|
| | Mz | R | BG | O | L | M | SB | S | | Mz | R | BG | O | L | M | SB | S | Mz | R | BG | O | L | M | SB | S |
| 87 | | | | | | 3 | | | 5 | 3 | | 4 | 2 | 4 | 7 | 6 | 4 | | | | | | | | |
| | | | | | | | | | 1 | | | | | | 4 | 3 | | | | | | | | | |
| 88 | 6 | | 6 | 5 | 5 | 8 | 9 | 7 | 5 | 5 | | 9 | 5 | 5 | 8 | 8 | 9 | 7 | 3 | 5 | 4 | 4 | 8 | 6 | 6 |
| | | | | | | | | | 1 | 2 | | 6 | 4 | 4 | 7 | 8 | 8 | 4 | | 4 | | | 6 | 2 | |
| 89 | 9 | 6 | 5 | 6 | 6 | 9 | 9 | 9 | 5 | 4 | | 9 | 4 | 6 | 8 | 9 | 8 | 8 | 6 | 9 | 4 | 5 | 9 | 9 | 9 |
| | | | | | | | | | 1 | 2 | | 5 | | 7 | 8 | 7 | 7 | 7 | 2 | 3 | 2 | 2 | 8 | 7 | 7 |
| 90 | 9 | 9 | 8 | 7 | 7 | 9 | 9 | | 5 | 8 | 4 | 9 | 8 | 7 | 8 | 9 | 9 | 9 | 8 | 9 | 9 | 9 | 9 | 9 | 9 |
| | | | | | | | | | 1 | 3 | | 8 | 6 | 6 | 8 | 9 | 8 | 7 | 6 | 8 | 6 | 6 | 9 | 9 | 8 |
| 91 | 7 | 7 | 8 | 7 | 6 | 7 | 9 | 5 | 5 | 7 | 6 | 9 | 7 | 7 | 8 | 9 | 9 | 7 | 5 | 8 | 6 | 7 | 9 | 9 | 7 |
| | | | | | | | | | 1 | 5 | 2 | 8 | 6 | 7 | 8 | 9 | 8 | 5 | 2 | 6 | 4 | 6 | 9 | 9 | 5 |
| 92 | 7 | 6 | 8 | 7 | 6 | 7 | 9 | 5 | 5 | 6 | 5 | 9 | 6 | 7 | 8 | 9 | 9 | 5 | 4 | 8 | 6 | 7 | 9 | 9 | 9 |
| | | | | | | | | | 1 | 6 | 5 | 8 | 5 | 7 | 7 | 9 | 8 | 2 | | 7 | 5 | 6 | 9 | 9 | 5 |
| 93 | 3 | | | | 5 | 6 | 4 | 7 | 5 | 4 | | 2 | 2 | 5 | 7 | 7 | 8 | 3 | | 2 | | | 6 | 4 | 5 |
| | | | | | | | | | 1 | * | * | * | * | * | * | * | * | * | * | * | * | * | * | * | * |
| 94 | 7 | 8 | 7 | 6 | 5 | 7 | 8 | 8 | 5 | 7 | 6 | 8 | 7 | 6 | 7 | 9 | 9 | 7 | 6 | 7 | 6 | 6 | 8 | 9 | 7 |
| | | | | | | | | | 1 | 2 | 3 | 7 | 6 | 6 | 7 | 8 | 8 | 6 | 5 | 7 | 4 | 4 | 8 | 8 | 6 |
| 95 | 7 | 7 | 6 | 6 | 6 | 7 | 8 | 7 | 5 | 4 | 4 | 9 | 3 | 6 | 7 | 7 | 9 | 7 | 4 | 8 | 7 | 3 | 8 | 7 | 7 |
| | | | | | | | | | 1 | 2 | 3 | 2 | | 5 | 6 | 7 | 8 | 5 | | 2 | 2 | 2 | 7 | 6 | 2 |
| 96 | | | | 3 | 5 | 6 | 7 | | 5 | 5 | | 4 | | 5 | 7 | 6 | 9 | 5 | | 4 | | 3 | 6 | 5 | 7 |
| | | | | | | | | | 1 | | | | | 3 | 6 | 5 | 5 | | | | | | 2 | 2 | |
| 97 | 7 | 6 | 7 | 7 | 5 | 8 | 9 | 8 | 5 | 7 | 3 | 8 | 7 | 6 | 7 | 8 | 9 | 7 | 5 | 8 | 6 | 5 | 8 | 9 | 8 |
| | | | | | | | | | 1 | 4 | 1 | 7 | 2 | 5 | 6 | 7 | 8 | 6 | 2 | 2 | 2 | 4 | 7 | 8 | 3 |
| 98 | 5 | | 6 | | 4 | 6 | 6 | | 5 | 4 | | 6 | 3 | 3 | 7 | 8 | 7 | 6 | | 6 | | | 8 | 7 | |
| | | | | | | | | | 1 | 2 | | | | 2 | 6 | 7 | 4 | 2 | | | | | 6 | 6 | |
| 99 | 4 | | 3 | 2 | 3 | 6 | 4 | 6 | 5 | 5 | | 8 | 4 | 5 | 8 | 8 | 8 | 7 | 3 | 7 | 6 | 4 | 7 | 7 | 6 |
| | | | | | | | | | 1 | | | 3 | 2 | 4 | 7 | 6 | 7 | 3 | | 2 | | 2 | 2 | 4 | |
| 100 | 7 | 6 | 7 | 7 | 7 | 8 | 9 | 8 | 5 | 6 | 4 | 9 | 7 | 7 | 9 | 9 | 8 | 6 | 4 | 7 | 7 | 9 | 9 | 9 | 8 |
| | | | | | | | | | 1 | 2 | 1 | 7 | 6 | 7 | 9 | 7 | 8 | 5 | 2 | 6 | 6 | 9 | 9 | 9 | 7 |
| 101 | 4 | | | | 4 | 5 | 6 | 6 | 5 | 3 | | 8 | 3 | 4 | 7 | 8 | 8 | 6 | | 4 | | | 9 | 8 | 5 |
| | | | | | | | | | 1 | 1 | | | | 2 | 6 | 8 | 8 | | | | | | 7 | 8 | 2 |
| 102 | 7 | 6 | 7 | 7 | 7 | 8 | 9 | 8 | 5 | 5 | 4 | 8 | 6 | 7 | 8 | 9 | 8 | 6 | 6 | 9 | 7 | 4 | 9 | 9 | 8 |
| | | | | | | | | | 1 | 2 | 4 | 7 | 5 | 6 | 7 | 8 | 8 | 6 | 5 | 7 | 6 | 2 | 8 | 9 | 7 |
| 103 | 8 | 8 | 7 | 7 | 6 | 7 | 7 | 8 | 5 | 4 | 4 | 9 | 9 | 7 | 8 | 9 | 8 | 7 | 5 | 9 | 9 | 8 | 9 | 9 | 9 |
| | | | | | | | | | 1 | 2 | 3 | 8 | 6 | 6 | 8 | 8 | 8 | 6 | 2 | 9 | 6 | 4 | 8 | 9 | 8 |
| 104 | 4 | | | | 3 | 6 | 6 | 6 | 5 | 4 | | 5 | 4 | 6 | 7 | 9 | 8 | 7 | | 5 | 2 | 3 | 7 | 8 | 6 |
| | | | | | | | | | 1 | | | 2 | | 2 | 6 | 8 | 8 | 2 | | | | | 6 | 7 | 2 |
| 105 | * | * | * | * | * | * | * | * | 5 | 4 | 4 | 9 | 6 | 6 | 7 | 9 | 8 | 7 | 5 | 9 | 4 | 5 | 9 | 9 | 9 |
| | | | | | | | | | 1 | 2 | 2 | 4 | 2 | 5 | 7 | 8 | 7 | 4 | 2 | 7 | | 4 | 7 | 8 | 7 |
| 106 | 4 | | 6 | | 3 | 2 | | | 5 | 5 | 3 | 8 | 4 | 6 | 7 | 9 | 6 | 6 | 5 | 4 | 3 | | 7 | 6 | 3 |
| | | | | | | | | | 1 | 2 | 2 | 6 | 2 | 5 | 6 | 9 | 5 | 2 | 2 | | | | 6 | 5 | |
| 107 | 6 | | 3 | 3 | 1 | 5 | 6 | | 5 | 3 | | 7 | 4 | 5 | 7 | 9 | 5 | 4 | | 5 | 6 | 3 | 7 | 7 | |
| | | | | | | | | | 1 | 2 | | 6 | 2 | 4 | 6 | 8 | 4 | | | 2 | | 2 | 7 | 5 | |
| 108 | | | | | 4 | 6 | 7 | 5 | 5 | | | | | 4 | 6 | 7 | 6 | | | | | | 5 | 6 | |
| | | | | | | | | | 1 | * | * | * | * | * | * | * | * | * | * | * | * | * | * | * | * |
| 109 | 6 | | 3 | 4 | 5 | 5 | 2 | 3 | 5 | 5 | 3 | 9 | 5 | 6 | 9 | 9 | 8 | 6 | 5 | 7 | 3 | 2 | 9 | 9 | 4 |
| | | | | | | | | | 1 | 2 | | 2 | 2 | 5 | 7 | 8 | 6 | 4 | 2 | 2 | | | 7 | 8 | 2 |
| 110 | * | * | * | * | * | * | * | * | 5 | 6 | 3 | 8 | 6 | 6 | 8 | 9 | 8 | 7 | 6 | 9 | 4 | 5 | 9 | 9 | 8 |
| | | | | | | | | | 1 | 4 | | 7 | 5 | 5 | 7 | 9 | 8 | 7 | 5 | 9 | 2 | 2 | 8 | 9 | 6 |
| 111 | 7 | | 4 | | 3 | 8 | 7 | 6 | 5 | 5 | | 8 | 6 | 7 | 8 | 9 | 8 | 7 | 4 | 9 | 6 | 5 | 9 | 9 | 7 |
| | | | | | | | | | 1 | 2 | | 5 | 2 | 6 | 7 | 9 | 7 | 5 | | 6 | 2 | 2 | 8 | 9 | 2 |
| 112 | 7 | 3 | 8 | 6 | 5 | 7 | 7 | 6 | 5 | 7 | | 9 | 6 | 7 | 8 | 9 | 8 | 8 | 5 | 9 | 6 | 5 | 9 | 9 | 9 |
| | | | | | | | | | 1 | 4 | | 7 | 5 | 6 | 8 | 8 | 8 | 7 | 2 | 6 | 2 | 2 | 9 | 9 | 7 |
| 113 | | | | | 3 | 6 | | 5 | 5 | 4 | | 8 | 4 | 6 | 8 | 9 | 7 | 4 | | 6 | | 5 | 6 | 7 | 6 |
| | | | | | | | | | 1 | 2 | | 1 | | 5 | 7 | 7 | 7 | 2 | | 2 | | | 2 | 5 | 2 |
| 114 | | | | | 5 | 4 | 3 | 4 | 5 | 3 | | 7 | 6 | 3 | 7 | 9 | 5 | | | | | | 6 | 4 | |
| | | | | | | | | | 1 | * | * | * | * | * | * | * | * | * | * | * | * | * | * | * | * |
| 115 | 7 | | 3 | 2 | 4 | 6 | 4 | 6 | 5 | 5 | 4 | 8 | 6 | 7 | 8 | 9 | 8 | 7 | 1 | 6 | 2 | 2 | 8 | 9 | 8 |
| | | | | | | | | | 1 | 4 | | 4 | 4 | 6 | 7 | 9 | 8 | 5 | | 4 | | 2 | 7 | 8 | 7 |
| 116 | | | 6 | | 5 | 6 | 4 | 5 | 5 | 4 | | 7 | 6 | 8 | 9 | 9 | 7 | 4 | | 7 | | 6 | 9 | 9 | 7 |
| | | | | | | | | | 1 | 2 | | 2 | 4 | 7 | 8 | 9 | 7 | 2 | | 6 | | 5 | 7 | 9 | 7 |
| 117 | | | | | | 4 | 2 | | 5 | 5 | 2 | 8 | 4 | 6 | 9 | 9 | 7 | | | 4 | | | 6 | 5 | |
| | | | | | | | | | 1 | 4 | | 4 | 2 | 5 | 8 | 8 | 6 | | | | | | 5 | 2 | |
| 118 | | | | | | 5 | | | 5 | 5 | | 4 | 2 | 6 | 8 | 9 | 7 | 2 | | 2 | 3 | 3 | 7 | 6 | 3 |
| | | | | | | | | | 1 | 2 | | 2 | | 4 | 7 | 7 | 5 | | | | | 2 | 5 | 2 | |
| 120 | 5 | 2 | 5 | 2 | 5 | * | 4 | 2 | 5 | 5 | | 7 | | 6 | 7 | 9 | 7 | 6 | | 6 | | 3 | 5 | 4 | 3 |
| | | | | | | | | | 1 | 3 | | | | 5 | 6 | 7 | 6 | | | 2 | | 1 | 5 | 3 | |
| 122 | 7 | * | * | * | * | * | * | * | 5 | 4 | | 9 | 2 | 5 | 7 | 9 | 6 | 5 | 2 | 6 | 2 | 2 | 3 | 7 | |
| | | | | | | | | | 1 | | | 2 | | 4 | 6 | 4 | 5 | | | | | | 3 | 6 | |
| 124 | * | * | * | * | * | * | * | * | 5 | | | | | 1 | 3 | 4 | 4 | | | | | | | | |
| | | | | | | | | | 1 | | | | | | 1 | 2 | 1 | | | | | | | | |
| 125 | | | | | | | | | 5 | | | 3 | 2 | 6 | 6 | 6 | 4 | | | | | | | | |
| | | | | | | | | | 1 | | | | | 1 | 3 | | | | | | | | | | |
| 126 | | | | | | | | | 5 | | | 2 | | 3 | 6 | 6 | 5 | | | | | | | | |
| | | | | | | | | | 1 | | | | | 1 | 5 | 4 | 4 | | | | | | | | |
| 133 | 7 | 6 | 7 | 5 | 5 | 7 | 7 | 4 | 5 | 7 | 4 | 7 | 3 | 7 | 9 | 9 | 8 | 7 | 3 | 5 | 3 | 4 | 9 | 8 | 3 |
| | | | | | | | | | 1 | 5 | 2 | 5 | | | 7 | 8 | 7 | 5 | | 2 | 1 | 2 | 8 | 7 | |
| 134 | | | | | | | | | 5 | 3 | | 4 | | 5 | 7 | 6 | 5 | | | | | | | | |

TABLE X-continued

| Compound of Ex. No. | Soil drench 10 kg/ha | | | | | | | | Dosage kg/ha | Foliar spray | | | | | | | | Pre-emergence | | | | | | | |
|---|---|---|---|---|---|---|---|---|---|---|---|---|---|---|---|---|---|---|---|---|---|---|---|---|---|
| | Mz | R | BG | O | L | M | SB | S | | Mz | R | BG | O | L | M | SB | S | Mz | R | BG | O | L | M | SB | S |
| | | | | | | | | | 1 | * | * | * | * | * | * | * | * | * | * | * | * | * | * | * | * |
| 135 | 6 | | 4 | 1 | | 6 | 5 | 2 | 5 | 3 | 2 | 9 | 6 | 7 | 8 | 8 | 7 | 6 | 2 | 7 | 4 | 5 | 8 | 9 | 4 |
| | | | | | | | | | 1 | 2 | | 7 | 4 | 5 | 7 | 6 | 7 | 2 | | 3 | | | 6 | 2 | |
| 136 | 8 | 8 | 8 | 8 | 7 | 7 | 9 | 8 | 5 | 9 | 7 | 9 | 9 | 8 | 9 | 9 | 8 | 9 | 8 | 9 | 9 | 7 | 9 | 9 | 3 |
| | | | | | | | | | 1 | 7 | 4 | 8 | 7 | 7 | 8 | 9 | 8 | 8 | 7 | 9 | 8 | 2 | 9 | 8 | 1 |
| 137 | 8 | 7 | 8 | 7 | 7 | 7 | 8 | 7 | 5 | 8 | 4 | 9 | 8 | 8 | 8 | 9 | 9 | 7 | 7 | 9 | 8 | 7 | 9 | 9 | 7 |
| | | | | | | | | | 1 | 6 | 2 | 9 | 6 | 7 | 8 | 9 | 8 | 5 | 3 | 8 | 6 | 5 | 9 | 9 | 2 |
| 138 | | | | | 1 | 2 | | | 5 | 3 | 1 | 6 | 4 | 4 | 8 | 9 | 8 | | | | | | | | |
| | | | | | | | | | 1 | 3 | 1 | 3 | 3 | 3 | 7 | 9 | 8 | | | | | | | | |
| 139 | | | | | | | | | 5 | 3 | 1 | 7 | 4 | 6 | 8 | 9 | 8 | | | | | | | | |
| | | | | | | | | | 1 | 3 | 1 | 6 | 4 | 5 | 8 | 9 | 8 | | | | | | | | |
| 140 | | | | | | | | | 5 | 4 | | 3 | | | 6 | 9 | 6 | | | | | | | | |
| | | | | | | | | | 1 | | | | | | 5 | 7 | 5 | | | | | | | | |
| 141 | 4 | | 4 | | | 6 | | | 5 | 2 | | 3 | 2 | 4 | 7 | 6 | 5 | | | | | | | | |
| | | | | | | | | | 1 | * | * | * | * | * | * | * | * | * | * | * | * | * | * | * | * |
| 142 | 7 | 6 | 8 | 6 | 4 | 7 | 8 | 8 | 5 | * | * | * | * | * | * | * | * | * | * | * | * | * | * | * | * |
| | | | | | | | | | 1 | | | 4 | 3 | 6 | 6 | 8 | 7 | | | | | | 6 | 2 | |
| 143 | * | * | * | * | * | * | * | * | 5 | | | 4 | | 2 | 6 | 4 | | | | | | | | | |
| | | | | | | | | | 1 | | | | | | | | | | | | | | | | |
| 144 | | | | | | | | | 5 | | | | | 3 | 6 | 2 | | | | | | | | | |
| | | | | | | | | | 1 | | | | | | 2 | | | | | | | | | | |
| 145 | 7 | 7 | 8 | 7 | 4 | 7 | 9 | 7 | 5 | 8 | 4 | 9 | 4 | 7 | 8 | 9 | 9 | 7 | 5 | 9 | 6 | 6 | 8 | 8 | 6 |
| | | | | | | | | | 1 | 6 | 2 | 8 | 3 | 6 | 7 | 9 | 8 | 6 | 2 | 8 | 3 | 5 | 7 | 8 | 2 |
| 146 | 7 | 6 | 7 | 3 | 6 | 5 | 6 | 8 | 5 | 5 | | 6 | 4 | 7 | 7 | 9 | 9 | 7 | 2 | 6 | 4 | 5 | 7 | 9 | 6 |
| | | | | | | | | | 1 | | | 2 | 1 | 5 | 7 | 9 | 9 | 2 | | 2 | | 2 | 4 | 5 | |
| 147 | 7 | 8 | 6 | 5 | 3 | 6 | 7 | 7 | 5 | 5 | 4 | 9 | 3 | 6 | 7 | 8 | 9 | 8 | 6 | 7 | 5 | 4 | 9 | 8 | 6 |
| | | | | | | | | | 1 | 2 | | 5 | | 2 | 7 | 7 | 7 | 4 | | 4 | 1 | 2 | 6 | 6 | |
| 148 | | | | | | | | | 5 | 5 | | 6 | 5 | 2 | 7 | 6 | 4 | | | | | | | | |
| | | | | | | | | | 1 | 2 | | 5 | 2 | | 5 | | 2 | | | | | | | | |
| 149 | 7 | 6 | 5 | 6 | 4 | 6 | 4 | 7 | 5 | 6 | 5 | 9 | 4 | 6 | 7 | 9 | 8 | 8 | 7 | 7 | 5 | 4 | 7 | 7 | 4 |
| | | | | | | | | | 1 | 2 | | 5 | 2 | 4 | 7 | 8 | 7 | 2 | | 6 | | | 2 | 6 | 2 |
| 150 | 8 | 2 | 5 | 2 | | 6 | | | 5 | 6 | | 5 | 4 | 5 | 7 | 8 | 6 | 7 | | 2 | | | 8 | 4 | |
| | | | | | | | | | 1 | 4 | | 2 | | 4 | 7 | 7 | 3 | 4 | | | | | 6 | 2 | |
| 151 | 7 | 6 | 7 | 7 | 5 | 6 | 9 | 6 | 5 | 7 | 4 | 9 | 7 | 6 | 8 | 8 | 8 | 7 | 5 | 8 | 4 | 4 | 9 | 9 | 6 |
| | | | | | | | | | 1 | 2 | | 7 | 4 | 4 | 7 | 8 | 7 | 6 | 4 | 6 | 2 | 2 | 8 | 7 | 4 |
| 152 | 7 | 7 | 7 | 7 | 5 | 7 | 8 | 6 | 5 | 7 | | 7 | 5 | 6 | 7 | 8 | 7 | 7 | 6 | 7 | 6 | 7 | 9 | 9 | 6 |
| | | | | | | | | | 1 | 4 | | 6 | 4 | 5 | 7 | 8 | 6 | 7 | 2 | 5 | 4 | 3 | 8 | 8 | 2 |
| 153 | | | | | 2 | 4 | 3 | | 5 | 4 | | 6 | 4 | 5 | 8 | 8 | 7 | | | | | | | | |
| | | | | | | | | | 1 | 2 | | 5 | | 4 | 8 | 7 | 6 | | | | | | | | |
| 154 | | | | | | | | | 5 | 4 | | 3 | 2 | 4 | 6 | 8 | 6 | | | | | | | | |
| | | | | | | | | | 1 | 2 | | 1 | | 4 | 6 | 8 | 5 | | | | | | | | |
| 155 | 6 | 5 | 6 | 2 | 6 | 4 | 3 | 2 | 5 | 5 | | 7 | 4 | 6 | 7 | 9 | 8 | 8 | 6 | 9 | 4 | 5 | 9 | 9 | 8 |
| | | | | | | | | | 1 | 2 | | 6 | 2 | 5 | 7 | 9 | 8 | 7 | 2 | 5 | 2 | 5 | 9 | 8 | 2 |
| 156 | 7 | 7 | 6 | 7 | 6 | 8 | 8 | 7 | 5 | 7 | 5 | 9 | 7 | 7 | 9 | 9 | 8 | 8 | 6 | 9 | 7 | 9 | 9 | 9 | 8 |
| | | | | | | | | | 1 | 5 | 5 | 7 | 5 | 6 | 8 | 8 | 8 | 7 | 5 | 9 | 6 | 8 | 9 | 9 | 6 |
| 157 | 8 | 7 | 7 | 8 | 6 | 8 | 8 | 8 | 5 | 7 | 4 | 9 | 8 | 7 | 8 | 8 | 8 | 7 | 8 | 9 | 8 | 7 | 9 | 9 | 8 |
| | | | | | | | | | 1 | 5 | | 7 | 2 | 6 | 7 | 7 | 8 | 7 | 7 | 9 | 6 | 5 | 9 | 9 | 7 |
| 158 | 4 | | 6 | 4 | 2 | 7 | 6 | 6 | 5 | 5 | 3 | 9 | 6 | 7 | 9 | 9 | 8 | 7 | 4 | 6 | 4 | 6 | 9 | 9 | 6 |
| | | | | | | | | | 1 | 4 | | 7 | 4 | 6 | 8 | 9 | 6 | 2 | | 5 | | 2 | 7 | 6 | 2 |
| 159 | 5 | | 4 | | 2 | 4 | 2 | 1 | 5 | 5 | 2 | 8 | 5 | 6 | 8 | 9 | 6 | 5 | | 6 | 3 | 2 | 7 | 5 | 4 |
| | | | | | | | | | 1 | 2 | 1 | 7 | 2 | 5 | 7 | 8 | 6 | 2 | | 2 | | 1 | 7 | 2 | 2 |
| 160 | 7 | 7 | 7 | 6 | 5 | 7 | 7 | 6 | 5 | 7 | 5 | 9 | 8 | 6 | 9 | 9 | 8 | 7 | 7 | 9 | 8 | 8 | 9 | 9 | 6 |
| | | | | | | | | | 1 | 5 | 2 | 8 | 6 | 5 | 9 | 9 | 8 | 7 | 2 | 9 | 7 | 5 | 9 | 9 | 2 |
| 161 | 7 | 5 | 7 | 7 | 4 | 4 | 9 | 6 | 5 | 6 | 4 | 9 | 7 | 6 | 9 | 9 | 8 | 6 | 6 | 9 | 7 | 5 | 9 | 9 | 8 |
| | | | | | | | | | 1 | 5 | 2 | 8 | 6 | 5 | 9 | 9 | 7 | 5 | 4 | 9 | 6 | 2 | 9 | 9 | 7 |
| 162 | 7 | 4 | 7 | 6 | 3 | 9 | 7 | 4 | 5 | 7 | 4 | 9 | 7 | 6 | 9 | 9 | 8 | 7 | 7 | 9 | 6 | 5 | 9 | 9 | 8 |
| | | | | | | | | | 1 | 5 | 2 | 8 | 7 | 5 | 9 | 9 | 8 | 6 | 5 | 8 | 2 | 2 | 9 | 9 | 8 |
| 163 | 4 | | 3 | 2 | 3 | 5 | 2 | 4 | 5 | 4 | | 9 | 6 | 6 | 9 | 9 | 7 | 5 | | 9 | 2 | 2 | 9 | 8 | 4 |
| | | | | | | | | | 1 | 2 | | 8 | 5 | 2 | 8 | 9 | 6 | | | 6 | | | 7 | 7 | |
| 164 | | | | | | 4 | 2 | | 5 | 6 | | 6 | 4 | 4 | 8 | 9 | 2 | | | | | 3 | 6 | 4 | |
| | | | | | | | | | 1 | | | 4 | 2 | 3 | 7 | 8 | 2 | | | | | 2 | 2 | 2 | |
| 165 | | | | | | 4 | 6 | | 5 | 4 | | 9 | 5 | 3 | 8 | 9 | 6 | | | 4 | | | 6 | 7 | |
| | | | | | | | | | 1 | 2 | | 4 | 2 | 2 | 7 | 8 | 5 | | | 2 | | | 5 | 2 | |
| 166 | | | | | | | | | 5 | 4 | 2 | 6 | 4 | 6 | 8 | 9 | 6 | | | 7 | | 4 | 7 | 7 | 4 |
| | | | | | | | | | 1 | 3 | | 2 | 2 | 5 | 8 | 8 | 5 | | | 7 | | 2 | 7 | 7 | |
| 167 | | | 6 | 3 | 4 | 3 | 4 | 2 | 5 | 6 | | 7 | 3 | 7 | 9 | 9 | 7 | | | 5 | 3 | 2 | 6 | 6 | 2 |
| | | | | | | | | | 1 | 2 | | 4 | 2 | 5 | 8 | 8 | 6 | | | 3 | | | 6 | 2 | |
| 168 | 4 | | 2 | | | 3 | 2 | 4 | 5 | 5 | | 6 | 2 | 3 | 9 | 5 | 6 | | | | | | 6 | | |
| | | | | | | | | | 1 | 2 | | 5 | | 1 | 8 | 2 | 5 | | | | | | 6 | | |
| 169 | | | | | | | | | 5 | 4 | | 3 | 3 | 4 | 8 | 9 | 5 | | | | | | 2 | 2 | |
| | | | | | | | | | 1 | 2 | | | | 3 | 8 | 8 | 4 | | | | | | 2 | | |
| 170 | 8 | 6 | 7 | 7 | 7 | 9 | 9 | 8 | 5 | 8 | 4 | 9 | 8 | 7 | 9 | 9 | 8 | 9 | 8 | 9 | 9 | 9 | 9 | 9 | 8 |
| | | | | | | | | | 1 | 7 | 2 | 8 | 7 | 7 | 9 | 9 | 8 | 8 | 7 | 9 | 8 | 7 | 9 | 9 | 8 |
| 171 | 7 | 7 | 8 | 8 | 2 | 9 | 9 | 8 | 5 | 9 | 7 | 9 | 8 | 7 | 9 | 9 | 8 | 9 | 9 | 9 | 9 | 6 | 9 | 9 | 9 |
| | | | | | | | | | 1 | 7 | 5 | 9 | 6 | 6 | 9 | 9 | 8 | 8 | 5 | 9 | 7 | 5 | 9 | 9 | 6 |
| 175 | 4 | | 2 | | | 2 | 3 | | 5 | 1 | | 6 | 2 | 5 | 7 | 7 | 5 | | | | | | 3 | 5 | |
| | | | | | | | | | 1 | | | 2 | | 4 | 5 | 5 | 2 | | | | | | | | |
| 176 | | | | | | | | | 5 | 3 | 4 | 6 | 2 | 4 | 8 | 8 | 6 | | | | | | | | |

TABLE X-continued

| Compound of Ex. No. | Soil drench 10 kg/ha | | | | | | | | Dosage kg/ha | Foliar spray | | | | | | | | Pre-emergence | | | | | | | |
|---|---|---|---|---|---|---|---|---|---|---|---|---|---|---|---|---|---|---|---|---|---|---|---|---|---|
| | Mz | R | BG | O | L | M | SB | S | | Mz | R | BG | O | L | M | SB | S | Mz | R | BG | O | L | M | SB | S |
| 177 | | | | | | | | | 1 | | | 3 | | 6 | 7 | 3 | | | | | | | | | |
| | | | | | | | | | 5 | 5 | | 4 | | 6 | 8 | 9 | 6 | | | | | | | | |
| 178 | 3 | | 4 | | 2 | 5 | 4 | | 1 | 3 | | 2 | | 4 | 7 | 8 | 5 | | | | | | | | |
| | | | | | | | | | 5 | 4 | | 6 | 2 | 6 | 8 | 8 | 7 | 6 | | 2 | | | | 7 | 7 |
| 179 | | | | | | | | | 1 | 1 | | | | 5 | 6 | 4 | 6 | | | | | | | | |
| | | | | | | | | | 5 | 4 | | 5 | 2 | 3 | 7 | 8 | 6 | | | | | | | | |
| 180 | | | | | | | | | 1 | | | 2 | | 2 | 4 | 4 | 2 | | | | | | | | |
| | | | | | | | | | 5 | 4 | | 5 | | 3 | 7 | 8 | 6 | | | | | | | | |
| 181 | | | | | | | | | 1 | 1 | | 2 | | 2 | 6 | 7 | 3 | | | | | | | | |
| | | | | | | | | | 5 | 6 | | 6 | 2 | 6 | 9 | 9 | 7 | | | | | | | | |
| 182 | 5 | 3 | 6 | 2 | | 5 | 4 | | 1 | 4 | | 2 | | 5 | 6 | 7 | 2 | | | | | | | | |
| | | | | | | | | | 5 | 6 | 3 | 8 | 2 | 7 | 9 | 9 | 7 | 4 | | 5 | 3 | 3 | 8 | 8 | |
| 183 | 6 | 4 | 6 | 4 | 6 | 7 | 8 | 7 | 1 | 5 | | 5 | | 5 | 7 | 9 | 5 | 1 | | 1 | | 1 | 7 | 7 | |
| | | | | | | | | | 5 | 6 | | 7 | 2 | 7 | 8 | 9 | 8 | 7 | 6 | 7 | | 3 | 8 | 7 | 4 |
| 184 | | | | | | | | | 1 | 4 | | 2 | | 6 | 7 | 9 | 8 | 5 | 2 | 6 | | 1 | 7 | 6 | |
| | | | | | | | | | 5 | 3 | 1 | 5 | 1 | 2 | 6 | 3 | 7 | | | | | | | | |
| 185 | 6 | 2 | 6 | 5 | 4 | 7 | 2 | 6 | 1 | 2 | | 2 | | | 2 | 1 | 4 | | | | | | | | |
| | | | | | | | | | 5 | 5 | | 7 | 3 | 6 | 7 | 8 | 8 | 7 | | 7 | 6 | 3 | 7 | 4 | 6 |
| 186 | | | | 4 | 3 | 5 | 4 | 5 | 1 | 2 | | 2 | | 2 | 6 | 6 | 6 | 5 | | 2 | | | 6 | | 2 |
| | | | | | | | | | 5 | 3 | | 4 | 3 | 2 | 7 | 8 | 6 | | 2 | | 4 | 2 | 6 | 7 | 4 |
| 187 | | | | | | 3 | | | 1 | | | 2 | | | 6 | 6 | 5 | | | | | | 4 | 6 | |
| | | | | | | | | | 5 | 4 | 3 | 5 | | 3 | 5 | 6 | 5 | 3 | | 2 | | | 5 | 3 | |
| 188 | 5 | 2 | 4 | | | 5 | 6 | 2 | 1 | 2 | | | | 2 | 2 | 2 | | | | | | | 2 | | |
| | | | | | | | | | 5 | 5 | | 8 | 4 | 4 | 7 | 9 | 6 | 5 | | 7 | | | 9 | 9 | |
| 189 | | | | | | | | | 1 | 2 | | 7 | 2 | 3 | 6 | 8 | 2 | 2 | | 2 | | | 7 | 7 | |
| | | | | | | | | | 5 | 5 | | 7 | 3 | 5 | 7 | 9 | 7 | 5 | | 4 | | | 7 | 3 | |
| 190 | 1 | | | | | 3 | | 2 | 1 | 2 | | 2 | | 2 | 7 | 8 | 6 | | | | | | 2 | | |
| | | | | | | | | | 5 | 4 | 2 | 7 | 4 6 | 8 | 9 | 8 | 6 | 5 | 3 | 4 | 7 | 5 | 5 | | |
| 191 | | | | | | 6 | | 4 | 1 | 2 | | | | 4 | 7 | 6 | 7 | | | | | | 2 | | |
| | | | | | | | | | 5 | 4 | | 3 | | 5 | 7 | 9 | 9 | | | | | | 5 | 3 | |
| | | | | | | | | | 1 | 2 | | | | 4 | 7 | 8 | 7 | | | | | | 2 | | |

What is claimed is:

1. A compound having the formula:

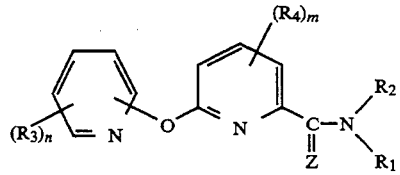

wherein;
a) R₁ and R₂ are selected from the group consisting of;
  i) hydrogen, alkyl, aryl, alkenyl, alkynyl, cycloalkyl, cycloalkylalkyl, aralkyl, alkaryl, hydroxy, alkoxy, alkenyloxy, alkynloxy, alkylcarbonyl, alkoxycarbonyl, amino, monoalkylamino, dialkylamino, derivatives thereof having one or more alkyl, alkenyl, alkynyl, cycloalkyl, heterocyclic groups wherein one or more hetero atoms are nitrogen, heterocyclic groups wherein one or more hetero atoms are oxygen, arylamino, halogen substituted arylamino groups, dialkylcarbamoyl, trialkylsilyl, naphthyl groups, and aryl moieties substituted by a member of the group consisting of
  halogens, hydroxy, cyano, alkyl, alkoxy, alkylthio, alkoxycarbonyl, aryl, aryloxy, monoalkylamino, and dialkylamino groups; or
  ii) R₁ and R₂ together form a chain consisting of alkenylene, alkylene and alkyl substituted alkylenes;
b) R₃ is selected from the group consisting of hydrogen, halogen, alkyl, alkoxy, aryl, aryloxy and aryloxy groups having at least one substituent selected from the group consisting of
  halogen, cyano, hydroxy, alkoxy, carboxy, alkoxy carbonyl, (alkylthio)carbonyl, alkylcarbonyl, amido, alkylamido, nitro, alkenyloxy, alkynloxy, alkylthio, haloalkylthio, alkenylthio, alkynylthio, alkylsulphinyl, alkylsulphonyl, alkyloximinoalkyl, and alkenyloximinoalkyl groups;
c) R₄ is selected from the group consisting of halogen, alkyl, and haloalkyl groups;
d) z is selected from the group consisting of oxygen and sulphur;
e) m is from 0 to 3; and
f) n is from 1 to 4.

2. The compound of claim 1 wherein the R₁, R₂, R₃ and R₄ independently are alkyl, alkenyl or alkynyl of up to 12 carbon atoms; any cycloalkyl group has from 3 to 6 carbon ring atoms; and any alkenylene or alkylene chain has from 3 to 6 chain members.

3. The compound of claim 1 wherein m is 0.

4. The compound of claim 1 wherein Z represents an oxygen atom.

5. The compound of claim 1 wherein
  a) R₁ is selected from the group consisting of $C_{1-6}$ alkyl, $C_{1-6}$ alkoxy, $C_{2-7}$ alkynyl, $C_{2-6}$ alkenyl, $C_{2-6}$ alkenyloxy, aryl, halogen substituted aryl, aralkyl, $C_{3-6}$ cycloalkyl, substituted ($C_{3-6}$ cycloalkyl)alkyl, furfuryl, substituted isoxazolyl, dialkylaminoalkyl, naphthyl, and trimethylsilyl groups;
  b) R₂ is hydrogen or a substituted $C_{1-6}$ alkyl; and
  c) R₃ is selected from the group consisting of hydrogen, halogen, $C_{1-6}$ alkyl, and $C_{1-6}$ haloalkyl groups.

6. The compound of claim 5 wherein said $C_{1-6}$ alkyl group is a $C_{1-5}$ alkyl group substituted by a member of the group consisting of alkoxy groups, aryloxy groups, cyano groups, and halogen atoms.

7. A compound having the formula:

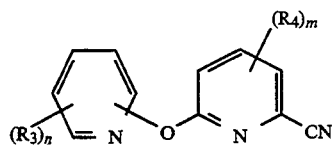

wherein
R$_3$ is selected from the group consisting of hydrogen, halogen, alkyl, alkoxy, aryl, aryloxy and aryloxy groups having at least one substitutent selected from the group consisting of halogen, cyano, hydroxy, alkoxy, carboxy, alkoxy carbonyl, (alkylthio)carbonyl, alkycarbonyl, amido, alkylamido, nitro, alkenyloxy, alkynloxy, alkylthio, haloalkylthio, alkenylthio, alkynylthio, alkylsulphinyl, alklsulphonyl, alkyloximinoalkyl, and alkenyloximinoalkyl groups; R$_4$ is selected from the group consisting of halogen, alkyl, and haloalkyl groups, m is from 0 to 3, and n is from 1 to 4.

8. A herbicidal composition comprising the compound of claim 1, together with at least one carrier.

9. The composition of claim 8, which comprises at least two carriers, at least one of which is a surface-active agent.

10. A method of combatting undesired plant growth at a locus, which comprises treating the locus with a compound of formula I as claimed in any one of claims 1-3 or 5-7 or with a composition as claimed in claim 2 or 9.

11. A method of inhibiting the growth of undesired plants comprising applying a herbicidal preparation of one of the members of the group consisting of the compound of claim 1, the compound of claim 7, and the composition of claim 8 to a locus of desired plant growth.

12. The method of claim 11 wherein the herbicidal preparation is formed by combining one of the members of the group consisting of the compound of claim 1, the compound of claim 7, and the composition of claim 8 with at least one carrier.

* * * * *

UNITED STATES PATENT AND TRADEMARK OFFICE
CERTIFICATE OF CORRECTION

PATENT NO. : 5,371,061

DATED : Dec. 6, 1994

INVENTOR(S) : Hans-Joachim Bissinger, et al

It is certified that error appears in the above-indentified patent and that said Letters Patent is hereby corrected as shown below:

Columns 19-22, Table X, should read as follows: (Examples 12 - 48).

Signed and Sealed this

Thirtieth Day of May, 1995

BRUCE LEHMAN

Attest:

Attesting Officer

Commissioner of Patents and Trademarks

TABLE X

| Compound of Ex. No. | Soil drench 10 kg/ha | | | | | | | | Dosage kg/ha | Foliar spray | | | | | | | | Pre-emergence | | | | | | | |
|---|---|---|---|---|---|---|---|---|---|---|---|---|---|---|---|---|---|---|---|---|---|---|---|---|---|
| | Mz | R | BG | O | L | M | SB | S | | Mz | R | BG | O | L | M | SB | S | Mz | R | BG | O | L | M | SB | S |
| 12 | 7 | 7 | 8 | 8 | 5 | 7 | 8 | 3 | 5 | 7 | 5 | 9 | 5 | 7 | 8 | 9 | 7 | 5 | 4 | 8 | 6 | 8 | 9 | 9 | 6 |
| | | | | | | | | | 1 | 5 | 2 | 8 | 4 | 7 | 8 | 8 | 7 | 2 | 2 | 6 | 5 | 4 | 6 | 8 | 2 |
| 13 | 5 | 3 | 6 | 3 | 2 | 5 | 5 | 2 | 5 | 6 | 4 | 9 | 5 | 6 | 9 | 9 | 8 | 2 | 2 | 6 | 1 | 3 | 6 | 7 | |
| | | | | | | | | | 1 | 4 | 2 | 9 | 4 | 6 | 9 | 9 | 6 | 1 | 1 | 4 | 1 | 1 | 4 | 5 | |
| 14 | 3 | | 4 | 1 | | 4 | 3 | | 5 | 2 | 1 | 8 | 3 | 6 | 8 | 9 | 6 | 3 | | | | | 3 | 3 | |
| | | | | | | | | | 1 | 2 | | 7 | 1 | 5 | 8 | 8 | 5 | | | | | | 3 | 2 | |
| 15 | | | 5 | | | 3 | 3 | | 5 | 3 | 2 | 8 | 2 | 6 | 8 | 8 | 7 | | | 2 | | 3 | 6 | 4 | 2 |
| | | | | | | | | | 1 | 1 | 1 | 7 | 1 | 4 | 8 | 7 | 6 | | | | | | 2 | 2 | 2 |
| 16 | 4 | 2 | 4 | 2 | 1 | 6 | 2 | 2 | 5 | 5 | 1 | 8 | 4 | 6 | 9 | 9 | 7 | | | 1 | | 2 | 6 | 4 | 2 |
| | | | | | | | | | 1 | 2 | | 7 | 2 | 5 | 9 | 9 | 6 | | | | | 2 | 2 | 1 | |

- 39 -

TABLE X (continued)

| Compound of Ex. No. | Soil drench 10 kg/ha | | | | | | | | Dosage kg/ha | Foliar spray | | | | | | | | Pre-emergence | | | | | | | |
|---|---|---|---|---|---|---|---|---|---|---|---|---|---|---|---|---|---|---|---|---|---|---|---|---|---|
| | Mz | R | BG | O | L | M | SB | S | | Mz | R | BG | O | L | M | SB | S | Mz | R | BG | O | L | M | SB | S |
| 17 | 7 | 7 | 8 | 7 | 6 | 7 | 7 | 2 | 5 | 6 | 5 | 8 | 5 | 8 | 9 | 9 | 8 | 5 | 5 | 6 | 6 | 4 | 8 | 8 | 3 |
|    |   |   |   |   |   |   |   |   | 1 |   | 5 | 8 | 4 | 7 | 9 | 9 | 8 |   | 5 | 3 | 2 | 2 | 6 | 6 | 2 |
| 18 | 6 | 6 | 7 | 6 | 5 | 5 | 6 | 4 | 5 | 5 | 5 | 8 | 7 | 7 | 9 | 9 | 7 | 3 | 1 | 6 | 1 | 2 | 7 | 4 | 1 |
|    |   |   |   |   |   |   |   |   | 1 | 4 | 5 | 8 | 4 | 7 | 9 | 9 | 7 | 2 |   | 2 | 1 | 1 | 4 | 2 |   |
| 19 | 7 | 6 | 7 | 6 | 4 | 5 | 7 | 2 | 5 | 5 | 5 | 8 | 6 | 7 | 9 | 9 | 7 | 4 | 2 | 4 | 5 | 3 | 7 | 7 | 2 |
|    |   |   |   |   |   |   |   |   | 1 | 4 | 2 | 7 | 3 | 7 | 9 | 9 | 7 | 3 |   | 2 | 3 | 1 | 5 | 4 |   |
| 20 |   | 4 |   | 3 | 2 |   |   |   | 5 | 4 | 3 | 6 | 4 | 6 | 9 | 9 | 6 |   |   |   |   |   | 4 |   |   |
|    |   |   |   |   |   |   |   |   | 1 | 2 | 2 | 3 | 2 | 5 | 8 | 7 | 5 |   |   |   |   |   | 2 |   |   |
| 21 | * | * | * | * | * | * | * | * | 5 | 3 |   |   |   |   | 5 | 2 | 3 |   |   |   |   |   |   |   |   |
|    |   |   |   |   |   |   |   |   | 1 |   |   |   |   |   | 2 | 2 | 1 |   |   |   |   |   |   |   |   |

TABLE X (continued)

| Compound of Ex. No. | Soil drench 10 kg/ha | | | | | | | | Dosage kg/ha | Foliar spray | | | | | | | | Pre-emergence | | | | | | | |
|---|---|---|---|---|---|---|---|---|---|---|---|---|---|---|---|---|---|---|---|---|---|---|---|---|---|
| | Mz | R | BG | O | L | M | SB | S | | Mz | R | BG | O | L | M | SB | S | Mz | R | BG | O | L | M | SB | S |
| 22 | 4 | 2 | 5 | 2 | 4 | 1 | 3 | | 5 | 5 | 2 | 8 | 5 | 5 | 9 | 9 | 8 | 5 | 2 | 5 | 2 | 2 | 7 | 7 | |
| | | | | | | | | | 1 | 5 | | 8 | 5 | 5 | 9 | 9 | 7 | 1 | | 3 | | 7 | 7 | |
| 23 | 4 | 2 | 6 | | 4 | | 5 | | 5 | 5 | 4 | 8 | 5 | 6 | 9 | 9 | 7 | 3 | | 4 | 1 | 3 | 8 | 9 | |
| | | | | | | | | | 1 | 4 | 1 | 8 | 5 | 6 | 8 | 9 | 7 | 1 | | 1 | 1 | 1 | 7 | 7 | |
| 24 | | | | | | | | | 5 | 5 | 3 | 7 | 4 | 4 | 9 | 9 | 7 | 3 | | 2 | 1 | 1 | 6 | 5 | |
| | | | | | | | | | 1 | 2 | | 6 | 3 | 4 | 8 | 9 | 6 | 1 | | 2 | | 6 | 6 | 4 | |
| 25 | 6 | 2 | 3 | 2 | 4 | 6 | 5 | 5 | 5 | 4 | | 9 | 4 | 7 | 9 | 9 | 8 | 7 | 5 | 7 | 4 | 2 | 9 | 9 | 3 |
| | | | | | | | | | 1 | 2 | | 8 | 4 | 6 | 9 | 9 | 7 | 5 | | 6 | | 8 | 8 | 8 | |
| 26 | | | | | | | | | 5 | 3 | | 2 | 1 | 1 | 4 | 3 | 2 | | | | | | | | |
| | | | | | | | | | 1 | 1 | | 1 | 1 | 1 | 4 | | | | | | | | | | |

TABLE X (continued)

| Compound of Ex. No. | Soil drench 10 kg/ha | | | | | | | | Dosage kg/ha | Foliar spray | | | | | | | | Pre-emergence | | | | | | | |
|---|---|---|---|---|---|---|---|---|---|---|---|---|---|---|---|---|---|---|---|---|---|---|---|---|
| | Mz | R | BG | O | L | M | SB | S | | Mz | R | BG | O | L | M | SB | S | Mz | R | BG | O | L | M | SB | S |
| 27 | | | | | | | | | 5 | 4 | 5 | 5 | 2 | 5 | 8 | 8 | 6 | | | | | | 4 | | |
| | | | | | | | | | 1 | 2 | 2 | 3 | 1 | 3 | 7 | 6 | 4 | | | | | | 2 | | |
| 28 | 5 | 5 | 6 | 6 | 2 | 3 | 3 | 4 | 5 | 8 | 4 | 8 | 5 | 7 | 9 | 9 | 8 | 4 | | 5 | | 2 | 5 | 6 | 3 |
| | | | | | | | | | 1 | 5 | 2 | 7 | 3 | 7 | 9 | 9 | 7 | | | | | 1 | 3 | 3 | |
| 29 | 5 | 5 | 7 | 5 | | 4 | 6 | 1 | 5 | 8 | 5 | 8 | 7 | 7 | 8 | 9 | 7 | 4 | 2 | 5 | | 3 | 6 | 4 | |
| | | | | | | | | | 1 | 6 | 4 | 7 | 3 | 6 | 8 | 9 | 7 | 2 | | 2 | | 1 | 4 | 2 | |
| 30 | 6 | 5 | 6 | 5 | 3 | 6 | 8 | 4 | 5 | 6 | 4 | 8 | 4 | 7 | 9 | 9 | 8 | 3 | | 5 | | 2 | 8 | 8 | 7 |
| | | | | | | | | | 1 | 4 | 2 | 6 | 2 | 6 | 9 | 9 | 8 | 1 | | 4 | | | 7 | 8 | 2 |
| 31 | 9 | 9 | 8 | 7 | 8 | 9 | 9 | 8 | 5 | 8 | 7 | 9 | 7 | 8 | 9 | 9 | 8 | 9 | 9 | 9 | 9 | 9 | 9 | 9 | 9 |
| | | | | | | | | | 1 | 5 | 4 | 8 | 5 | 8 | 9 | 9 | 8 | 9 | 9 | 8 | 9 | 9 | 9 | 9 | 9 |

- 42 -

TABLE X (continued)

| Compound of Ex. No. | Soil drench 10 kg/ha | | | | | | | | Dosage kg/ha | Foliar spray | | | | | | | | Pre-emergence | | | | | | | |
|---|---|---|---|---|---|---|---|---|---|---|---|---|---|---|---|---|---|---|---|---|---|---|---|---|---|
| | Mz | R | BG | O | L | M | SB | S | | Mz | R | BG | O | L | M | SB | S | Mz | R | BG | O | L | M | SB | S |
| 32 | 6 | 4 | 6 | 6 | 2 | 4 | 5 | | 5 | 8 | 6 | 9 | 7 | 8 | 9 | 9 | 8 | 6 | 3 | 7 | 6 | 7 | 9 | 8 | 4 |
| | | | | | | | | | 1 | 6 | 4 | 8 | 5 | 8 | 8 | 9 | 8 | 4 | 1 | 5 | 5 | 6 | 8 | 8 | |
| 33 | 2 | | 4 | 5 | 2 | 3 | * | 7 | 5 | 6 | 3 | 8 | 4 | 5 | 9 | 9 | 7 | 3 | 1 | 4 | 3 | 3 | 7 | 4 | 3 |
| | | | | | | | | | 1 | 3 | 1 | 6 | 3 | 5 | 8 | 8 | 6 | 1 | 1 | 1 | 1 | 1 | 7 | 1 | 1 |
| 34 | 7 | 5 | 7 | 3 | 7 | 9 | 9 | 7 | 5 | 3 | 3 | 9 | 6 | 8 | 8 | 8 | 8 | 5 | | 6 | 4 | 7 | 8 | 9 | 8 |
| | | | | | | | | | 1 | 1 | 1 | 4 | 4 | 5 | 8 | 7 | 6 | 1 | | | 3 | 3 | 7 | 5 | 3 |
| 35 | | | | | | | | | 5 | 2 | | 3 | | 5 | 8 | 8 | 5 | | | | | | | | |
| | | | | | | | | | 1 | 1 | | 2 | | 3 | 8 | 7 | 4 | | | | | | | | |
| 36 | 2 | 1 | 5 | | 6 | | 6 | | 5 | 4 | 3 | 7 | 3 | 6 | 9 | 9 | 6 | | | | | | 4 | | |
| | | | | | | | | | 1 | 1 | 1 | 5 | 1 | 5 | 8 | 9 | 6 | | | | | | 2 | | |

TABLE X (continued)

| Compound of Ex. No. | Soil drench 10 kg/ha | | | | | | | | Dosage kg/ha | Foliar spray | | | | | | | | Pre-emergence | | | | | | | |
|---|---|---|---|---|---|---|---|---|---|---|---|---|---|---|---|---|---|---|---|---|---|---|---|---|---|
| | Mz | R | BG | O | L | M | SB | S | | Mz | R | BG | O | L | M | SB | S | Mz | R | BG | O | L | M | SB | S |
| 37 | | | | | | | | | 5 | * | * | * | * | * | * | * | * | | | | | | 3 | | |
| | | | | | | | | | 1 | 2 | 2 | 2 | 1 | 3 | 8 | 8 | 5 | | | | | | 1 | | |
| 38 | | | | | | | | | 5 | 4 | | 5 | 2 | 5 | 7 | 9 | 5 | | | | | | | | |
| | | | | | | | | | 1 | | | 2 | | 3 | 6 | 7 | 3 | | | | | | | | |
| 39 | * | * | * | * | * | * | * | * | 5 | 4 | | 4 | 3 | 3 | 8 | 8 | 3 | | | | | | | | |
| | | | | | | | | | 1 | 2 | | | | | 6 | 3 | 2 | | | | | | | | |
| 40 | | | | | | | | | 5 | 2 | | 4 | 3 | 3 | 7 | 7 | 2 | | | | | | | | |
| | | | | | | | | | 1 | | | | | | 2 | 2 | 1 | | | | | | | | |
| 42 | | | | | | | | | 5 | 3 | | 3 | 1 | 3 | 7 | 6 | 4 | | | | | | | | |
| | | | | | | | | | 1 | 2 | | | | 1 | 4 | 2 | 2 | | | | | | | | |

TABLE X (continued)

| Compound of Ex. No. | Soil drench 10 kg/ha | | | | | | | | Dosage kg/ha | Foliar spray | | | | | | | | Pre-emergence | | | | | |
|---|---|---|---|---|---|---|---|---|---|---|---|---|---|---|---|---|---|---|---|---|---|---|---|
| | Mz | R | BG | O | L | M | SB | S | | Mz | R | BG | O | L | M | SB | S | BG | O | L | M | SB | S |
| 43 | 7 | 6 | 7 | 6 | 6 | 8 | 9 | 7 | 5 | 3 | 3 | 5 | 1 | 8 | 9 | 9 | 8 | 9 | 4 | 6 | 9 | 9 | 7 |
| | | | | | | | | | 1 | | 2 | 2 | | 6 | 9 | 8 | 6 | 5 | 2 | 2 | 8 | 9 | 2 |
| 44 | | | | | 1 | 5 | 6 | 4 | 5 | | | | | 2 | 4 | 3 | 3 | | | | 4 | 5 | 1 |
| | | | | | | | | | 1 | | | | | | | | 2 | | | | | 2 | |
| 45 | | | | | | | | | 5 | | | 2 | | 4 | 7 | 8 | 6 | | | | 3 | 3 | |
| | | | | | | | | | 1 | | | | | 1 | 5 | 4 | 4 | | | | | | |
| 46 | | | 5 | | 4 | 4 | 5 | 5 | 5 | 4 | 1 | 4 | 2 | 6 | 7 | 8 | 6 | 1 | | | 4 | 7 | 5 |
| | | | | | | | | | 1 | | | | | 2 | 4 | 5 | 5 | | | | 1 | 2 | 2 |
| 47 | 4 | 3 | 6 | 3 | 4 | 6 | 6 | 6 | 5 | 4 | 3 | 5 | 2 | 6 | 8 | 8 | 6 | 4 | 4 | 4 | 7 | 7 | 5 |
| | | | | | | | | | 1 | 1 | | 2 | | 5 | 7 | 6 | 6 | | 1 | 1 | 5 | 6 | 1 |

TABLE X (continued)

| Compound of Ex. No. | Soil drench 10 kg/ha | | | | | | | | Dosage kg/ha | Foliar spray | | | | | | | | Pre-emergence | | | | | | | |
|---|---|---|---|---|---|---|---|---|---|---|---|---|---|---|---|---|---|---|---|---|---|---|---|---|
| | Mz | R | BG | O | L | M | SB | S | | Mz | R | BG | O | L | M | SB | S | Mz | R | BG | O | L | M | SB | S |
| 48 | | | | | | | | | 5 | 4 | 1 | 1 | 2 | 4 | 6 | 9 | 4 | | | | | | | | |
| | | | | | | | | | 1 | 2 | | | 2 | 3 | 6 | 6 | 2 | | | | | | | | |
| 49 | 4 | | 5 | | 2 | 3 | | | 5 | 7 | | 6 | 4 | 6 | 7 | 9 | 6 | | | 3 | | | 3 | | |
| | | | | | | | | | 1 | 4 | | 5 | 1 | 6 | 7 | 9 | 5 | | | 1 | | | 1 | | |
| 50 | | | | | | | | | 5 | 5 | | 6 | 4 | 6 | 7 | 9 | 6 | | | | | 2 | 3 | 2 | 3 |
| | | | | | | | | | 1 | 2 | | 4 | 1 | 5 | 7 | 9 | 6 | | | | | 1 | 1 | 1 | 3 |
| 51 | | | | | | | | | 5 | 3 | 2 | 3 | 6 | 6 | 7 | 8 | 5 | | | | | 2 | 5 | 5 | 4 |
| | | | | | | | | | 1 | 1 | | 1 | 3 | 3 | 5 | 4 | 2 | | | | | 1 | 1 | 5 | 3 |
| 52 | | | | | | | | | 5 | 3 | | 3 | 5 | 5 | 9 | 9 | 6 | | | | | | | | |
| | | | | | | | | | 1 | 2 | | 2 | 2 | 2 | 7 | 6 | 4 | | | | | | | | |